United States Patent [19]

Maugh et al.

[11] Patent Number: 5,049,504

[45] Date of Patent: Sep. 17, 1991

[54] BIOADHESIVE CODING SEQUENCES

[75] Inventors: Kathy J. Maugh, Walnut, Calif.; David M. Anderson, Rockville, Md.; Robert Strausberg; Susan L. Strausberg, both of Silver Spring, Md.; Russ McCandliss, Gaithersburg, Md.; Tena Wei, Rockville, Md.; David Filpula, Gaithersburg, Md.

[73] Assignee: Genex Corporation, Gaithersburg, Md.

[21] Appl. No.: 530,449

[22] Filed: May 30, 1990

Related U.S. Application Data

[63] Continuation of Ser. No. 82,456, Aug. 7, 1987, abandoned, which is a continuation-in-part of Ser. No. 933,945, Nov. 24, 1986, abandoned, which is a continuation-in-part of Ser. No. 650,128, Sep. 13, 1984, abandoned.

[51] Int. Cl.$^5$ .................... C12N 1/21; C12N 15/12; C12N 1/19; C12N 15/63
[52] U.S. Cl. .................... 435/252.33; 435/172.3; 435/256; 435/320; 435/69.1; 536/27; 935/11; 935/69; 935/73; 530/350
[58] Field of Search .................... 435/69.1, 172.3, 320, 435/255, 252.33, 256; 530/328; 536/27; 935/11, 23, 28, 29, 69, 73

[56] References Cited

U.S. PATENT DOCUMENTS

| | | | |
|---|---|---|---|
| 4,546,082 | 10/1985 | Kurjan et al. | 435/172.3 |
| 4,585,585 | 4/1986 | Waite | 530/328 |
| 4,687,740 | 8/1987 | Waite | 435/68.1 |
| 4,721,673 | 1/1988 | Uren et al. | 435/183 |
| 4,798,791 | 1/1989 | Anderson et al. | 435/68.1 |

FOREIGN PATENT DOCUMENTS

| | | |
|---|---|---|
| 243818 | 11/1987 | European Pat. Off. |
| 1085400 | 4/1986 | Japan |

OTHER PUBLICATIONS

Garfinkel et al., *J. Mol. Biol.*, 168:765-789 (1983).
Scawen et al., *Biochem. J.*, 147; 343-349 (1975).
Suggs et al., *PNAS* (U.S.A.), 78 (11): 6613-6617 (1981).
Johnston et al., *PNAS* (U.S.A.) 79 (11): 6971-6975 (1982).
International Search Report for PCT/US88/00876 (May 16, 1988).
Johnson, R., *Gen. Engin. News* Apr. 1985, pp. 14 & 18.
Waite, J. H., *J. Comp. Physiol. B* 156:491-496 (1986).
Lindner, E. et al., *Chem. Abstr.* 87:179439w (1977).
Lindner, E. et al., *Proc. 3rd Int. Biodegradation Symp.* (1975), pub'd 1976, J. M. Sharpley et al., eds. Appl. Sci. U.K.
Cook, M. in *Adhesion in Biological Systems,* R. S. Manly, ed., Academic Press, N.Y., 1907, pp. 139-150.
Yamamoto, H., *J. Chem. Soc. Perkin Trans.* I:613-618 (1987).
Young, G. A. et al., Chapter 2 in "Adhesion 6", K. W. Allen, ed., Applied Science Publishers, London, 1982, pp. 19-39.
Walker, G., *J. Adhesion* 12:51-58 (1981).
Linder, E. et al. Report #69-3 from the Paint Laboratory of the San Fran. Bay Naval Shipyard at Vallejo, Ca.; Gov. Rep. Announce 71:77-78 (1971).
Bowen, H. J., *NIDR Symp. on Dental Adhesive Materials* (1973), pp. 82-93.

(List continued on next page.)

*Primary Examiner*—Richard A. Schwartz
*Assistant Examiner*—Mary E. Mosher
*Attorney, Agent, or Firm*—Sterne, Kessler, Goldstein & Fox

[57] ABSTRACT

Vectors are provided that are capable of expressing, in microbial transformants, a protein having the native amino acid sequence of a bioadhesive precursor protein of a marine animal selected from the group consisting of mussels, barnacles, and oysters. The bioadhesive precursor protein can be expressed in transformants, recovered and converted to a bioadhesive protein by hydroxylation.

30 Claims, 14 Drawing Sheets

OTHER PUBLICATIONS

Linder, E., *Proc. 5th Int. Cong. Marine Corrosion and Fouling: Marine Biology*, Barcelona (Spain), May 19–23, 1980, pp. 189–212.

Wake, W. C., Chapter 13 in: "Adhesion and the Formulation of Adhesives", 2nd Edition, Applied Science Publishers, New York (1982), pp. 256–266.

Waite, J. H. et al., *J. Biol. Chem.*, 258:2911–2915 (1983).

Waite, J. H. and Tanzer, M. L., *Science*, 212:1038–1040 (1981).

Marumo, K. and Waite, J. H., *Biochem. Biophys. Acta* 872:98–103 (1986).

Skujins, J. J. et al., *Arch. Biochem. Biophys.* 111:359–364 (1965).

Lerch, K. and Ettlinger, L., *Eur. J. Biochem.* 31:427–437 (1972).

Waite, J. H., *J. Mar. Biol. Assoc. U.K.* 65:359–371 (1985).

Gallop, P. M. and Seifter, S., *Meth. Enzymol.* VI:635–641 (1963).

Redl, H. and Schlog, G., *Facial Plastic Surgery* 2:315–321 (1985).

Waite, J. H., in *Mollusca*, vol. I:467–504 (1983).

Waite, J. H., et al., *Biochem.* 24:5010–5014 (1985).

Waite, J. H., *Biol. Rev.* 58:209–231 (1983).

FIG. 1

```
        Ala Leu Ala Leu Pro Pro Ala Pro Ala Phe Ala Pro Ala Leu Ala Pro Ala Pro Ala Pro Ala Pro Asn Pro Pro
     Ga GCA CTA GCA CTA CCG CCA GCA CCT GCT TTT GCA CCT GCT GCA CTT GCA CCG GCT CCT GCA CCT AAT CCT CCA
        Bsp1286                                                                      5                                              10                                              15                                              20                                              25                                              30
     Ser Pro Pro Ser Pro Pro Thr Pro Pro Thr Pro Pro Ala Pro Ala Pro Ser Pro Pro Ser Pro Pro Asn
     AGT CCT CCG AGT CCT CCG ACT CCA CCG ACT CCA CCG GCA CCG GCA CCG AGT CCA CCA CCG AGT CCT AAT
        35                                              40                                              45                                              50                                              55                                              60
     Pro Pro Ser Pro Pro Phe Pro Pro Phe Pro Pro Ser Pro Pro Ser Pro Pro Pro Pro Phe Pro Pro Thr
     CCA CCT CCG AGT CCA CCG TTT CCT CCG TTT CCT CCG AGT CCA CCG AGT CCA CCA CCA TTT CCT CCG ACT
        65                                              70                                              75                                              80                                              85                                              90
     Tyr Lys Ala Lys Pro Thr Asn Pro Ser Tyr Pro Pro Thr Tyr Lys Ile Lys Tyr Lys Ala Lys Pro Thr
     TAT AAA GCA AAG CCA ACT AAT CCT TCA AGT TAT CCT CCA ACT TAT AAA ATA AAG TAT AAA GCA AAG CCA ACT
        95                                              100                                             105                                             110                                             115                                             120
     Tyr Lys Ala Lys Pro Ser Tyr Pro Ser Tyr Pro Pro Thr Tyr Lys Ala Lys Tyr Lys Ala Lys Pro Thr
     TAT AAA GCA AAA CCA AGT TAT CCT TCA AGT TAT CCT CCA ACT TAT AAA GCA AAG TAT AAA GCA AAG CCA ACT
        125                                             130                                             135                                             140                                             145                                             150
     Tyr Lys Ala Lys Pro Thr Tyr Pro Pro Thr Tyr Pro Pro Thr Tyr Lys Ile Lys Pro Thr Tyr Lys Ala
     TAT AAA GCA AAA CCA ACG TAT CCT CCA ACT TAT CCA CCA ACT TAT AAA ATA AAG CCA ACT TAT AAA GCA
        155                                             160                                             165                                             170                                             175                                             180
     Pro Thr Asn Pro Ser Tyr Pro Pro Thr Tyr Lys Thy Tyr Pro Pro Thr Ser Tyr Pro Pro Thr Tyr Lys
     CCA ACT AAT CCT TCA AGT TAT CCT CCA ACG TAT AAA ACG TAT CCT CCA ACT TCA ACG TAT CCA ACT TAT AAA
        185                                             190                                             195                                             200                                             205                                             210
     Pro Ser Tyr Pro Pro Thr Tyr Pro Pro Thr Thr Tyr Lys Ala Lys Pro Thr Tyr Lys Ala Lys Tyr Lys
     CCA AGT TAT CCT CCA ACA TAT CCT CCA ACG TAT AAA GCA AAG TAT AAA GCA CCA ACT TAT AAA GCA TAT AAA
        215                                             220                                             225                                             230                                             235                                             240
     Ala Lys Pro Thr Tyr Lys Ala Lys Pro Lys Pro Lys Tyr Pro Lys Pro Thr Tyr Lys Pro Thr Tyr Lys
     GCA AAG CCA ACT TAT AAA GCA AAA CCA AAG CCA AAG TAT CCT AAG CCA ACA TAT AAA CCA ACA TAT AAA
        245                                             250                                             255                                             260                                             265                                             270
     Ser Lys Ser Ile Tyr Pro Ser Ser Tyr Lys Lys Thr Tyr Pro Lys Leu Lys Pro Tyr Pro Tyr Pro Tyr Lys
     TCC AAG TCA ATA TAT CCC TCT TCA TAG AAG ACT TAT CCC AAA CTA ACC TAT TTG TTA AAA TAT TCA AAA
        275                                             280                                             285                                             290                                             295                                             300
     Pro Lys Pro Ser Tyr Pro Pro Ser Tyr Lys Pro Lys Ile Thr Pro Ser Tyr Lys Pro Ser Tyr Pro Lys
     CCA AAG CCA AGT TAT CCT CCA TCA AGT TAT AAA CCT AAG ATT ACT TAT CCC TCA ACT TAT AAA CCA ACA TAC
        305                                             310                                             315                                             320                                             325                                             330
     Ser Lys Thr Ser Tyr Pro Thr Pro Tyr Asn Lys Lys Ile Ser Tyr Pro Ser Ala Lys Thr Ser Tyr Pro Ala Lys
     TCT AAA ACA AGT TAC CCT CCT ACA TAT AAC AAA AAG ATC AGC TAT CCA TCA TCA AAG ACA AGT TAT CCC GCA AAG
     Pro Thr Asn Arg Tyr ***
     CCA ACA AAC AGA TAT TAA TCT CAA TAT TAA AAG TAT TAA CTA AAA TAT TCA CAT TAC TGT ACT ACA CAT TTT AAC GTT TGT ATT GAT GAG
                     G   A*
                      BdI
     GAA CAG ATG AAC ATT TGA AAG TAA TAC ATA ATC GGG GTT AAT GAT TTG TTA TAT TCA ATC TTA ATA TGT TTG TGA TTT GTT ATG TTC TTG
     AAG TAT TGT TTC AAA TAA AAG TTT ATT CTT TTC TGG TAA AAA TAA AAA AAA AAA AAA AAA AAA AGA ATT C
                                                                                                                                                                                                                      EcoRI
```

FIG. 2

```
              5                  10                 15                 20
Tyr Lys Ala Lys Pro Ser Tyr Pro Pro Thr Tyr Lys Ala Lys Pro Thr Tyr Lys Ala Lys
TAT AAA GCA AAA CCA AGT TAT CCT CCA ACT TAT AAA GCA AAG CCA ACT TAT AAA GCA AAG 25                 30                 35                 40
Pro Thr Asn Pro Ser Thr Tyr Lys Ala Lys Pro Ser Tyr Pro Pro Thr Tyr Lys Ala Lys
CCA ACT AAT CCT TCA ACG TAT AAA GCA AAG CCA AGT TAT CCT CCA ACT TAT AAA GCA AAA 45                 50                 55                 60
Pro Ser Tyr Pro Pro Thr Tyr Lys Ala Lys Pro Ser Tyr Pro Pro Thr Tyr Lys Ala Lys
CCA AGT TAT CCT CCA ACT TAT AAA GCA AAA CCA AGT TAT CCT CCA ACG TAT AAA GCA AAG 65                 70                 75                 80
Pro Thr Tyr Lys Ala Lys Pro Thr Tyr Pro Ser Thr Tyr Lys Ala Lys Pro Thr Tyr Lys
CCA ACT TAT AAA GCA AAG CCA ACT TAT CCT TCA AGC TAT AAA GCA AAG CCA ACT TAT AAA 85                 90                 95                 100
Ala Lys Pro Thr Tyr Pro Pro Thr Tyr Lys Ala Lys Pro Ser Tyr Pro Pro Thr Tyr Lys
GCA AAG CCA ACT TAT CCT CCA ACT TAT AAA GCA AAA CCA AGT TAT CCT CCA ACA TAT AAA 105                110                115                120
Pro Lys Pro Ser Tyr Pro Pro Thr Tyr Lys Ser Lys Ser Ile Tyr Pro Ser Ser Tyr Lys
CCA AAG CCA AGT TAT CCT CCA ACT TAT AAA TCC AAG TCA ATA TAT CCC TCT TCA TAC AAA

125
Pro Lys Thr Tyr Pro Pro Thr Tyr
CCT AAG ACT TAT CCC CCA ACA TAT
```

FIG. 3

```
     5|                    10|                   15|                  20
Thr Ser Thr Tyr Lys Ala Lys Pro Ser Tyr Pro Pro Thr Tyr Lys Ala Lys Pro Thr Tyr
ACT TCA ACT TAT AAA GCA AAG CCA AGT TAT CCT CCA ACT TAT AAA GCA AAG CCA ACT TAC

25|                    30|                   35|                  40
Pro Ser Thr Tyr Lys Ala Lys Pro Ser Tyr Pro Pro Thr Tyr Lys Pro Lys Ile Ser Tyr
CCT TCA ACG TAT AAA GCA AAG CCA AGT TAT CCT CCA ACT TAT AAA CCT AAG ATA AGT TAT

45|                    50|                   55|                  60
Pro Pro Thr Tyr Lys Ala Lys Pro Ser Tyr Pro Pro Thr Tyr Lys Ala Lys Pro Ser Tyr
CCT CCA ACT TAT AAA GCA AAG CCA AGT TAT CCT CCA ACT TAT AAA GCA AAA CCA AGT TAT

65|                    70|                   75|                  80
Pro Pro Thr Tyr Lys Ala Lys Pro Thr Tyr Lys Ala Lys Pro Thr Asn Pro Ser Thr Tyr
CCT CCA ACT TAT AAA GCA AAG CCA ACT TAT AAA GCA AAG CCA ACT AAT CCT TCA ACG TAT

85|
Lys Ala Lys Pro Ser Tyr
AAA GCA AAG CCA AGT TAT
```

FIG. 4

```
     BamHI SmaI    EcoRI XbaI
CG |GATCCCC|GGG |AATT|CTAGA
```

FIGURE 5A

```
Restriction sites  ClaI                              NaeI         SphI
DNA                |CGATG GCG GCC GCG.......ACG CC|G GCA AGC ATG|
                   |TAC CGC CGG CGC........TGC GG|C CGT TC
TRANSLATION         MET ALA ALA ALA    THR  PRO ALA SER MET
```

FIGURE 5B

```
       10         20         30         40         50         60         70         80         90        100
   1 CCGAGGGTAA CAAAAAACA  ACAGCATAAA TAACCCGCT  CTTACACATT CCAGCCCTGA AAAGGGCAT  CAAATTAAAC CACACCTATG GTGTATGCAT
 101 TTATTGCAT  ACATTCAATC AATTGTTATC TAAGGAAATA CTTACATATG GTTCGTGCAA ACAAACGCAA CGAGGCTCTA CGAATCGATG CATGCAGCTG
 201 TCTAGAATTC CCGGGGATCC GTCGACCTGC AGGCAAGCTT ACTCCCCATC CCCTCCAGTA AACTCCATCT AACTCCATCG GGATTTGTTC AGAACGCTCG
 301 GTGCCGCCG  GGCGTTTTT  ATTGGTGAGA ATCGCAGCAA CTTGTCGCGC CAATCGAGCC ATGTCGTCGT CAACGACCCC CCATTCAAGA ACAGCAAGCA
 401 GCATTGAGAA CTTTGGAATC CAGTCCCTCT AGGGGTGCAC AGGGTGCAC  GCGCACTTTT ATCCGCCTCT GCTGCCCTCC GCCACCGTAG 501        520        530        540        550        560        570        580        590        600
 501 TTAAATTTAT GGTTGGTTAT GAAATGCTAG CAGAGACCCA CAGAGACCTG GCGAGAAAC  ACCGCAGAAC AGGCAGCAGA GCGTTTGCGC GCACTCAGCG ATACCCCGGT
 601 TGATAATCAG AAAAGCCCCA AAAACAGGAA GAAATGTATA GCAAATATTT AAATTGTAAA CGTTAATATT TGTTAAAAT  TCGCGTTAAA TTTTTGTTAA
 701 ATCAGCTCAT TTTTTAACCA ATAGGCCGAA ATCGGCAAAA TCCCTTATAA AATCAAAAGAA TCCCGAGA   TAGCCCGAGA TGTTGTTCCA GTTGGAACA 
 801 AGAGTCCACT ATTAAAGAAC GTGGACTCCA ACGTCAAAGG GCGAAAAACC GCCTATCAGG GCGATGGCCC ACTACGTGAA CCATCACCCA AATCAAGTTT
 901 TTTGGGGTCG AGGTGCCGTA AAGCACTAAA TCGGAACCCT AAAGGGAGCC CCCGATTTAG AGCTTGACGG GGAAAGCCGG CGAACGTGGC GAGAAAGGAA 1010       1020       1030       1040       1050       1060       1070       1080       1090       1100
1001 GGGAAGAAAG CGAAAGGAGC GGGCGCTAGG GCGCTGGCAA GTGTAGCGGT CACGCTGCGC GTAACCACCA CACCCGCCGC GCTTAATGCG CCGCTACAGG
1101 GCGCGTATCC ATTTTCGCGA ATCCGGAGTG TAAGAAATGA GCGCCCGCAC CGTTGAAGCT AAAACACAA  TCTCTGTTTG CCAACGCATT TGGCTACCCT GCCACTCACA
1201 CCATTCAGGT GCGTCATATA CTGACTGAAA ACGCCCGCAC CGAACTG    CGACCTGAAA CGAGATGGCG AGTTGATGCG
1301 GGAGTCTCAT GCCTCTATGC GCGTCATCAC CGAATCACC  CGAATCACC  CGAAATCACC TTGACACTCT GGTAGAAATC GTCAAAGCTG CAAAGGTGGC
1401 GTACGCATGA CCGGCGGGGG ATTTGGGCGG TGTATCGTCG CGCTGATCCG GGAAGAGCTG GTGCCTGCCG CACAGCAAGC CAATATGAAG 1510       1520       1530       1540       1550       1560       1570       1580       1590       1600
1501 CAAAACAGG  TATTAAGAG  ACTTTTTACG TTGTAAACC  ATCACAAGGA GCAGGACAGT GCTGAACGAA ACTCCCGCAC TGGCACCCGA TGGCAGCCGT
1601 ACGGACTGTT CTGCCTCGCG CGTTTCGGTG ATGACGGTGA AAACCTCTGA CACATGCAGC TCCCGGAGAC GGTCACAGCT TGTCTGTAAG CGGATGCCGG
1701 GAGCAGACAA GCCCGTCAGG GCGCGTCAGC GCGTGTTGGC GGGTGTCGGG GCGCAGCCAT GACCCAGTCA CGTAGCGATA GCGGAGTGTA TACTGGCTTA
1801 ACTATGCGGC ATCAGAGCAG ATTGTACTGA GAGTGCACCA TATGCGGTGT GAAATACCGC ACAGATGCGT AAGGAGAAAA TACCGCATCA GGCGCTCTTC
1901 CGCTTCCTCG CTCACTGACT CGCTGCGCTC GGTCGTTCGG CTGCGGCGAG CGGTATCAGC TCACTCAAAG GCGGTAATAC GTTATCCAC  AGAATCAGGG
```

```
           2010       2020       2030       2040       2050       2060       2070       2080       2090       2100
2001  GATAACGCAG GAAAGAACAT GTGAGCAAAA GGCCAGCAAA AGGCCAGGAA CCGTAAAAAG GCCGCGTTGC TGGCGTTTTT CCATAGGCTC CGCCCCCCTG
2101  ACGAGCATCA CAAAAATCGA CGCTCAAGTC AGAGGTGGCG AAACCCGACA GGACTATAAA GATACCAGGC GTTTCCCCCT GGAAGCTCCC TCGTGCGCTC
2201  TCCTGTTCCG ACCCTGCCGC TTACCGGATA CCTGTCCGCC TTTCTCCCTT CGGGAAGCGT GGCGCTTTCT CAATGCTCAC GCTGTAGGTA TCTCAGTTCG
2301  GTGTAGGTCG TTCGCTCCAA GCTGGGCTGT GTGCACGAAC CCCCCGTTCA GCCCGACCGC TGCGCCTTAT CCGGTAACTA TCGTCTTGAG TCCAACCCGG
2401  TAAGACACGA CTTATCGCCA CTGGCAGCAG CCACTGGTAA CAGGATTAGC AGAGCGAGGT ATGTAGGCGG TGCTACAGAG TTCTTGAAGT GGTGGCCTAA 2510       2520       2530       2540       2550       2560       2570       2580       2590       2600
2501  CTACGGCTAC ACTAGAAGGA CAGTATTTGG TATCTGCGCT CTGCTGAAGC CAGTTACCTT CGGAAAAAGA GTTGGTAGCT CTTGATCCGG CAAACAAACC
2601  ACGCTGGTA GCGGTGGTTT TTTTGTTTGC AAGCAGCAGA TTACGCGCAG AAAAAAAGGA TCTCAAGAAG ATCCTTTGAT CTTTTCTACG GGGTCTGACG
2701  CTCAGTGGAA CGAAAACTCA CGTTAAGGGA TTTTGGTCAT GAGATTATCA AAAAGGATCT TCACCTAGAT CCTTTTAAAT TAAAATGAA GTTTTAAATC
2801  AATCTAAAGT ATATATGAGT AAACTTGGTC TGACAGTTAC CAATGCTTAA TCAGTGAGGC ACCTATCTCA GCGATCTGTC TATTTCGTTC ATCCATAGTT
2901  GCCTGACTCC CCGTCGTGTA GATAACTACG ATACGGGAGG GCTTACCATC TGGCCCCAGT GCTGCAATGA TACCGCGAGA CCCACGCTCA CCGGCTCCAG 3010       3020       3030       3040       3050       3060       3070       3080       3090       3100
3001  ATTTATCAGC AATAAACCAG CCAGCCGGAA GGGCCGAGCG CAGAAGTGGT CCTGCAACTT TATCCGCCTC CATCCAGTCT ATTAATTGTT GCCGGGAAGC
3101  TAGAGTAAGT AGTTCGCCAG TTAATAGTTT GCGCAACGTT GTTGCCATTG CTACAGGCAT CGTGGTGTCA CGCTCGTCGT TTGGTATGGC TTCATTCAGC
3201  TCCGGTTCCC AACGATCAAG GCGAGTTACA TGATCCCCCA TGTTGTGCAA AAAAGCGGTT AGCTCCTTCG GTCCTCCGAT CGTTGTCAGA AGTAAGTTGG
3301  CCGCAGTGTT ATCACTCATG GTTATGGCAG CACTGCATAA TTCTCTTACT GTCATGCCAT CCGTAAGATG CTTTTCTGTG ACTGGTGAGT ACTCAACCAA
3401  GTCATTCTGA GAATAGTGTA TGCGGCGACC GAGTTGCTCT TGCCCGGCGT CAACACGGGA TAATACCGCG CCACATAGCA GAACTTTAAA AGTGCTCATC 3510       3520       3530       3540       3550       3560       3570       3580       3590       3600
3501  ATTGGAAAAC GTTCTTCGGG GCGAAAACTC TCAAGGATCT TACCGCTGTT GAGATCCAGT TCGATGTAAC CCACTCGTGC ACCCAACTGA TCTTCAGCAT
3601  CTTTTACTTT CACCAGCGTT TCTGGGTGAG CAAAAACAGG AAGGCAAAAT GCCGCAAAAA AGGGAATAAG GGCGACACGG AAATGTTGAA TACTCATACT
3701  CTTCCTTTTT CAATATTATT GAAGCATTTA TCAGGGTTAT TGTCTCATGA GCGGATACAT ATTTGAATGT ATTTAGAAAA ATAAACAAAT AGGGGTTCCG
3801  CGCACATTTC CCCGAAAAGT GCCACCTGAC GTCTAAGAAA CCATTATTAT CATGACATTA ACCTATAAAA ATAGGCGTAT CACGAGGCCC TTTCGTCTTC
3901  AAG
```

| 1 | 2 | 3 | 4 | 5 | 6 | 7 | 8 | 9 | 10 |
|---|---|---|---|---|---|---|---|---|---|
| $Ala_{46}$ | $Lys_{63}$ | $Pro_{48}$ | $Ser_{41}$ | $Tyr_{63}$ | $Pro_{63}$ | $Pro_{52}$ | $Thr_{60}$ | $Tyr_{61}$ | $Lys_{62}$ |
| $Pro_{16}$ | | $Lys_4$ | $Thr_{21}$ | | | $Ser_{11}$ | $Ser_2$ | $His_1$ | $Gly_1$ |
| $Thr_1$ | | $Leu_4$ | $Asn_1$ | | | | $Val_1$ | $Asp_1$ | |
| | | $Ile_3$ | | | | | | | |
| | | $Thr_1$ | | | | | | | |
| | | $Met_1$ | | | | | | | |
| | | $Ser_1$ | | | | | | | |
| | | $Ala_1$ | | | | | | | |

FIG. 10

BIOADHESIVE CODING SEQUENCES

This application is a continuation of application Ser. No. 07/082,456, filed Aug. 7, 1987, now abandoned, which is a continuation-in-part of application Ser. No. 933,945, filed Nov. 24, 1986, now abandoned, which is a continuation-in-part of application Ser. No. 650,128, filed Sept. 13, 1984, now abandoned.

BACKGROUND OF THE INVENTION

1. Field of the Invention

This invention relates to the production of bioadhesives that can be employed to bond substances for use in wet environments. Typically, the bioadhesives of the invention are employed as marine adhesives, biomedical adhesives or dental adhesives. The invention further relates to the microbial production of bioadhesive precursor proteins that can be converted to bioadhesives by chemical or enzymatic treatment.

2. Brief Description of Background Art

The properties of adhesives generally must be tailored to meet the requirements of the particular environments in which they are to be used. Ideally, an adhesive should be cured and it should maintain both its adhesivity and cohesivity under the conditions of use. Curing is the altering of the physical properties of an adhesive by chemical or enzymatic means. In the case of the bioadhesives produced by the procedures described herein, curing is likely to be due to the cross-linking of adjacent uncured adhesive molecules by catalytic and/or chemical agents. Curing may also involve adhesive cross-linking with the substrate.

Many adhesives that exhibit excellent adhesive properties under dry conditions suffer a substantial or total loss of those properties in wet environments. Furthermore, adhesives of the prior art cannot be cured in wet environments. Consequently, it has been particularly difficult to develop adhesives for use in wet environments, such as marine adhesives or adhesives for use in medical and dental applications.

Marine mussels and other sessile invertebrates have the ability to secrete adhesive substances by which they affix themselves to underwater objects. For example, mussels of the genus Mytilus, e.g., the species *Mytilus edulis* and *Mytilus californianus*, deposit an adhesive substance from the mussel foot that becomes cured, forming a permanent attachment to the substrate. A major component of the adhesive plaque deposited by *M. edulis* has been identified as a hydroxylated protein of about 130,000 daltons (Waite, J. H., *J. Biol. Chem.*, 258:2911-2915 (1983)). While this substance might make an excellent adhesive for use in wet environments, isolation of the uncured adhesive from mussels for commercial use is not practical, since the extraction of 1 kg of the adhesive substance would require the use of about 5 to 10 million mussels. Besides involving a very laborious process, great care would have to be taken, in case the adhesive were to be employed in medical applications, to insure that other mussel proteins and contaminants were removed from the bioadhesive prior to use in order to prevent antigenic or anaphylactic reactions.

U.S. Pat. No. 4,585,585 describes a procedure for preparing a bioadhesive polymer by chemically linking decapeptide units produced by the enzymatic digestion of isolated mussel adhesive protein. In accordance with the disclosure of that patent, a bioadhesive protein is first isolated from phenol glands of mussels of the genus Mytilus using the protein purification procedures described by Waite and Tanzer in *Science*, 212:1038 (1981). The isolated bioadhesive, having a molecular weight of 120,000 to 140,000 daltons, is first treated with collagenase, which reduces its molecular weight by about 10,000 daltons. The treated protein is then digested with trypsin, and the digested protein subjected to gel filtration dialysis to isolate decapeptides of the general formula

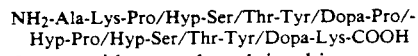

The decapeptides produced in this manner are then polymerized by the use of chemical linking groups such as glutaraldehyde, oligopeptides, amino acids or other bifunctional linking groups to produce bioadhesives containing up to about 1,000 such decapeptide units.

The procedure of U.S. Pat. No. 4,585,585 still requires the isolation of bioadhesive protein from mussel, which, as previously indicated, is impractical on a commercial scale. Moreover, in addition to the laborious purification procedure, this process adds the additional steps of enzymatic digestion, isolation of the decapeptide fragments and chemical reassemblage of the fragments into a bioadhesive polymer. This arduous procedure is not well-suited to commercial production. Further, the polymers produced by this method are quite different from the mussel adhesive since they contain only chemically polymerized decapeptides produced by trypsin digestion of the natural molecule. Analysis of the natural gene described herein demonstrates that there are other significant sequence elements in the mussel adhesive from *Mytilus edulis*.

Thus a need has continued to exist for means and methods for the efficient production of bioadhesives having the excellent properties associated with the mussel foot bioadhesive in wet environments.

A further need has continued to exist for means and methods for producing bioadhesives having the properties of the mussel foot adhesive without the necessity of handling and processing large quantities of mussels.

SUMMARY OF THE INVENTION

This invention involves application of the techniques of recombinant DNA technology to the production of bioadhesives of the type produced by marine animals such as mussels, barnacles and oysters. In particular, we have cloned genes for native bioadhesive precursor proteins (also termed polyphenolic proteins) of the mussel *Mytilus edulis* and constructed expression vectors capable of expressing these precursor proteins in microbial hosts. The bioadhesive precursor proteins are chemically or enzymatically hydroxylated, mimicking a process which occurs in vivo in the mussel, to produce a bioadhesive protein which cures to produce an adhesive having excellent properties in wet environments.

In the course of our work, we have isolated multiple cDNA clones coding for native *M. edulis* bioadhesive precursor proteins. Two of the encoded proteins (from cDNA isolates 14-1 and 52) have a common C-terminal sequence of 134 amino acids, including a hexapeptide followed by twelve decapeptides, ten of which display non-homology with the decapeptide sequence described in U.S. Pat. No. 4,585,585.

Another encoded protein, from cDNA isolate 55, has homology with 53 and 110 amino acids in the proteins encoded by cDNAs 14-1 and 52, as well as homology in a different region with 34 and 57 amino acids of the proteins encoded by cDNA isolates 56 and 52. The coding homologies are conserved at the DNA level. One likely explanation for these observations is that the *M. edulis* polyphenolic protein gene consists of several exons that can be spliced together in different combinations at the mRNA level. Alternatively, there could be several closely related genes.

This disclosure is not intended to be limiting to any one exon combination or bioadhesive precursor protein gene, as a method is described which allows the isolation and use of any existing gene or gene combinations. In all the unique decapeptide coding segments observed in the 4 cDNA clones described herein, 24 of 39 decapeptides display non-homology with the decapeptide described in U.S. Pat. No. 4,585,585.

Yet a further encoded protein, from cDNA isolate N1, a 2.1 kb clone, contains 76 continuous tandem repeats of decapeptides and hexapeptides. Of the 63 decapeptides in the N1 protein, 32 display non-homology with the decapeptide described in U.S. Pat. No. 4,585,585.

There is provided, in accordance with this invention, a DNA segment comprising codons for the native amino acid sequence of a bioadhesive precursor protein of a margine animal, e.g., of a mussel of the genus Mytilus, e.g., *M. edulis*.

```
AAG CTG TCA TCT TAC AAA CCT ATT AAG ACA ACA TAT AAT GCA AAG ACA AAT TAT CCA CCA

GTT TAT AAA CCT AAG ATG ACT TAT CCT CCT ACA TAC AAA CCA AAG CCC AGT TAT CCT CCA

ACA TAT AAA TCA AAG CCC ACA TAC AAA CCT AAG ATA ACA TAC CCT CCA ACT TAT AAA GCA

AAG CCC AGT TAT CCT CCA ACA TAT AAA CCT AAG AAA ACT TAT CCC CCC ACA TAT AAA CCT

AAA CTA ACC TAT CCT CCT ACA TAC AAA CCA AAG CCC AGT TAT CCT CCA ACA TAT AAA TCA

AAG CCC ACA TAC AAA CCT AAG ATA ACA TAC CCT CCA ACA TAT AAA GCA AAG CCA AGT TAT

CCT CCT ACA TAT AAA CCT AAG AAA ACT TAT CCC CCC ACA TAT AAA CCT AAA CTA ACC TAT

CCT CCT ACA TAT AAA CCA AAG GCC AGT TAT CCT CCA ACA TAT AAA CCA AAA CCA AGT TAT

CCC CCT TCA TAT AAA ACT AAG AAA ACT TAT CCC CCC ACA TAT AAA CCT AAA CTA ACC TAT

CCT CCT ACA TAT AAA CCA AAA CCA AGT TAT CCC CCT TCA TAC AAA CCT AAG AAA ACT TAT

CCC CCC ACA TAT AAA CCT AAA CTA ACC TAT CCT CCT ACA TAT AAA GCA AAG CCA AGT TAT

CCT CCA ACA TAT AAA GCA AAA CCA AGT TAT CCT CCA ACT TAT AAA GCA AAA CCA AGT TAT

CCT CCA ACA TAT AAA GCA AAA CCA AGT TAT CCT TCA ACT TAT AAA GCA AAA CCA AGT TAT

CCT CCA ACT TAT AAA GCA AAG CCA ACT TAT AAA GCA AAG CCA ACT TAT AAA GCA AAG CCA

ACT TAT CCT TCA ACG TAT AAA GCA AAG CCA ACT TAT CCT CCA ACT TAT AAA GCA AAA CCA

AGT TAT CCT CCA ACT TAT AAA GCA AAG CCA ACT TAT AAA GCA AAG CCA ACT TAT AAA GCA

AAG CCA AGT TAT CCT CCA ACT TAT AAA GCA AAA CCA AGT TAT CCT CCA ACT TAT AAA GCA

AAG CCA AGT TAT CCT CCA ACG TAT AAA GCA AAG CCA AGT TAT CCT CCA ACT TAT AAA GCA

AAA CCA AGT TAT CCT CCA ACT TAT AAA GTA AAG CCA ACA TAT AAA GCA AAA CCA ACT TAT

CCT TCA ACG TAT AAA GCA AAG CCA AGT TAT CCT CCA ACT TAT AAA GCA AAA CCA AGT TAT

CCT CCA ACT TAT AAA GCA AAA CCA AGT TAT CCT CCA ACG TAT AAA GCA AAA CCA AGT TAT

CCT CCA ACT TAT AAA GCA AAA CCA ACT TAT CCT TCA ACG TAT AAA GCA AAA CCA AGT TAT

CCT CCA ACT TAT AAA CCT AAA ATA AGT TAT CCT CCA ACT TAT AAA GCA AAA CCA AGT TAT

CCT TCA ACT TAT AAA GCA AAA TCA AGT TAT CCT CCA ACT TAT AAA GCA AAA CCA AGT TAT

CCT CCA ACT TAT AAA GCA AAG CCA ACT TAT CCT TCA ACG TAT AAA GCA AAG CCA ACT TAT

AAA GCA AAG CCA AGT TAT CCT CCA ACG TAT AAA GCA AAG CCA AGT TAT CCT CCA ACT TAT

AAA GCA AAA CCC AGT TAT CCT CCA ACT TAT AAA GCA AAG CCA ACT TAT AAA GCA AAG CCA

ACT TAT AAA GCA AAG CCA ACT TAT CCT TCA ACG TAT AAA GCA AAG CCA AGT TAT CCT CCA

ACT TAT AAA GCA AAA CCA AGT TAT CCT CCA ACT TAT AAA GCA AAA CCA AGT TAT CCT CCA

ACT TAT AAA GCA AAA CCA AGT TAT CCT CCA ACT TAT AAA GCA AAG CCA AGT TAT CCT CCA

ACG TAT AAA GCA AAG CCA AGT TAT CCT CCA ACT TAT AAA GCA AAA CCA AGT TAT CCT CCA

ACT TAT AAA GCA AAG CCA ACT TAT AAA GCA AAG CCA ACT TAT CCT TCA ACG TAT AAA GCA

AAG CCA AGT TAT CCT CCA ACT TAT AAA GCA AAA CCA AGT TAT CCT CCA ACT TAT AAA GCA

AAA CCA AGT TAT CCT CCA ACT TAT AAA GCA AAA CCA ACT TAT AAA GCA AAG CCA ACT TAT
```

-continued

CCT TCA ACG TAT AAA GCA AAA CCA AGT TAT CCT CCA ACT CAT AAA GCA AAA CCA ACT TAT

AAA GCA AAG CCA ACT TAT CCT TCA ACT TAT AAA GCA AAA CCA ACT TAT CCT TCA ACG GAT

GGA GCA AAA TCA, which code for the amino acid sequence:

Lys Leu Ser Ser Tyr Lys Pro Ile Lys Thr Thr Tyr Asn Ala Lys Thr Asn Tyr Pro Pro Val Tyr Lys Pro Lys Met Thr Tyr Pro Pro Thr

Tyr Lys Pro Lys Pro Ser Tyr Pro Pro Thr Tyr Lys Ser Lys Pro Thr Tyr Lys Pro Lys Ile Thr Tyr Pro Pro Thr Tyr Lys Ala Lys Pro

Ser Tyr Pro Pro Thr Tyr Lys Pro Lys Lys Thr Tyr Pro Pro Thr Tyr Lys Pro Lys Leu Thr Tyr Pro Pro Thr Tyr Lys Pro Lys Pro Ser

Tyr Pro Pro Thr Tyr Lys Ser Lys Pro Thr Tyr Lys Pro Lys Ile primer coating for an adhesive, to the surfaces being bonded.

There are also provided by the invention methods for bonding or wetting surfaces with composite materials including bioadhesive protein and other polymers and/or adhesives.

BRIEF DESCRIPTION OF THE DRAWINGS

FIG. 1 presents the DNA sequence and translated amino acid sequence of a gene identified as cDNA clone 14-1, which codes for a bioadhesive precursor protein of *M. edulis*. The asterisk denotes the BclI site introduced by ODM.

FIG. 2 presents the DNA sequence and translated amino acid sequence of a gene identified as cDNA clone 52, which codes for a bioadhesive precursor protein of *M. edulis*. The asterisk denotes the BclI site introduced by ODM.

FIG. 3 presents the DNA sequence and translated amino acid sequence of a gene identified as cDNA clone 55, which codes for a bioadhesive precursor protein of *M. edulis*.

FIG. 4 presents the DNA sequence and translated amino acid sequence of a gene identified as cDNA clone 56, which codes for a bioadhesive precursor protein of *M. edulis*.

FIG. 5(*a*) presents the sequence of a portion of a multi-restriction site region of plasmid pGX2627. FIG. 5(*b*) presents a DNA sequence and translated amino acid sequence of portions of a synthetic DNA segment employed in the construction of plasmid pGX2346 from plasmid pGX2287.

FIG. 7 is the DNA sequence of plasmid pGX2627. The length of pGX2627 is 3903 bases (circular, genome-plasmid pGX1066 with added M13 ori compliment). The composition of this sequence is 1040 A, 988 C, 961 G, and 914 T.

FIG. 9 presents the DNA sequence and translated amino acid sequence of a gene identified as cDNA clone Nl, which codes for a bioadhesive precursor protein of *M. edulis*.

FIG. 10 presents the amino acid variations in decapeptides of clone Nl. The variations in each position are shown, with the subscripts indicating the number of decapeptides in clone Nl in which the particular amino acid occurs at the position cited.

DETAILED DESCRIPTION OF THE PREFERRED EMBODIMENTS

Figure 6:
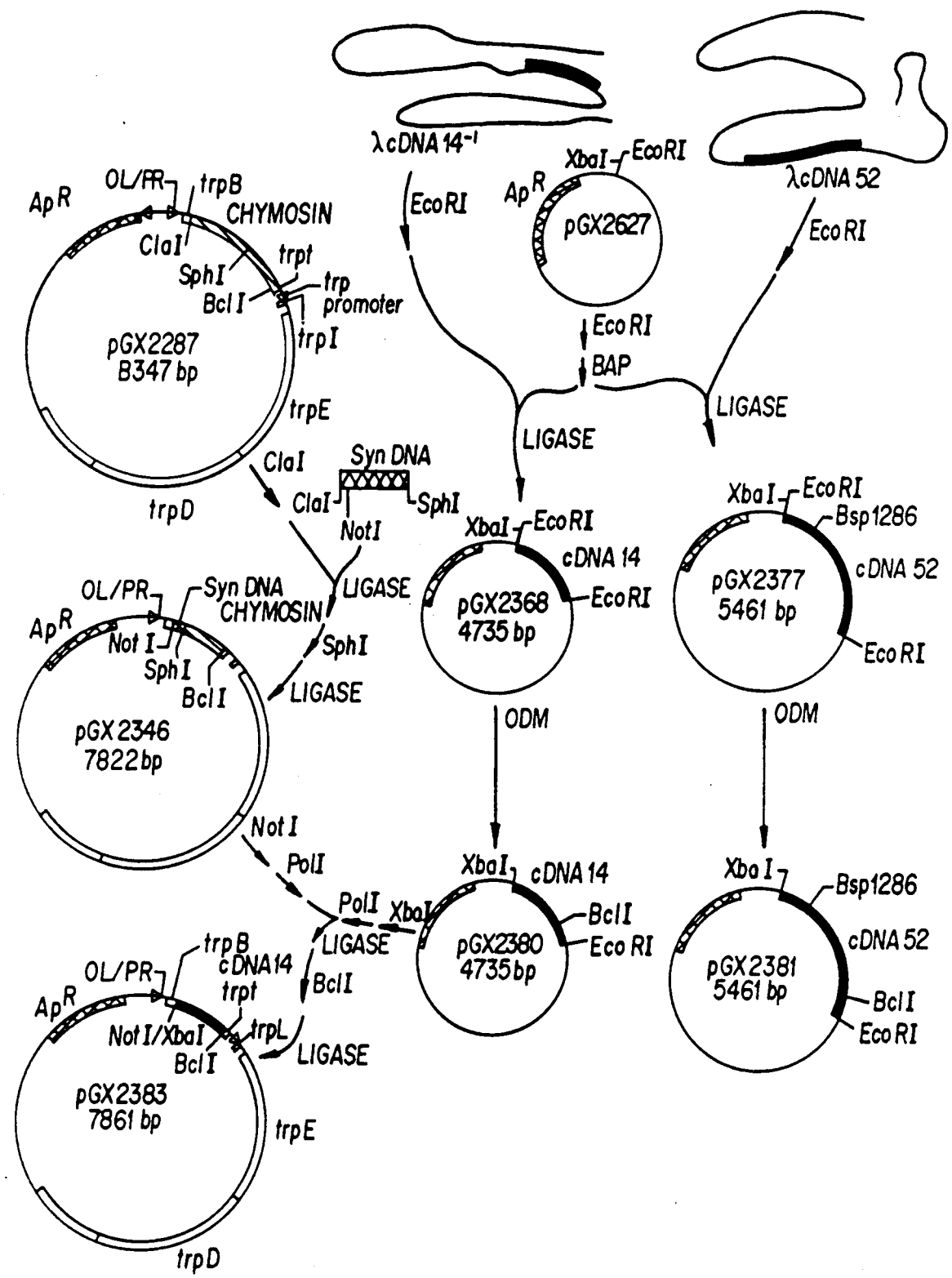
FIG. 6 is a schematic representation of the construction of plasmids pGX2346, pGX2368, pGX2377, pGX2380, pGX2381 and pGX2383. Plasmid pGX2383 is an expression vector for a bioadhesive precursor protein.
Figure 8:
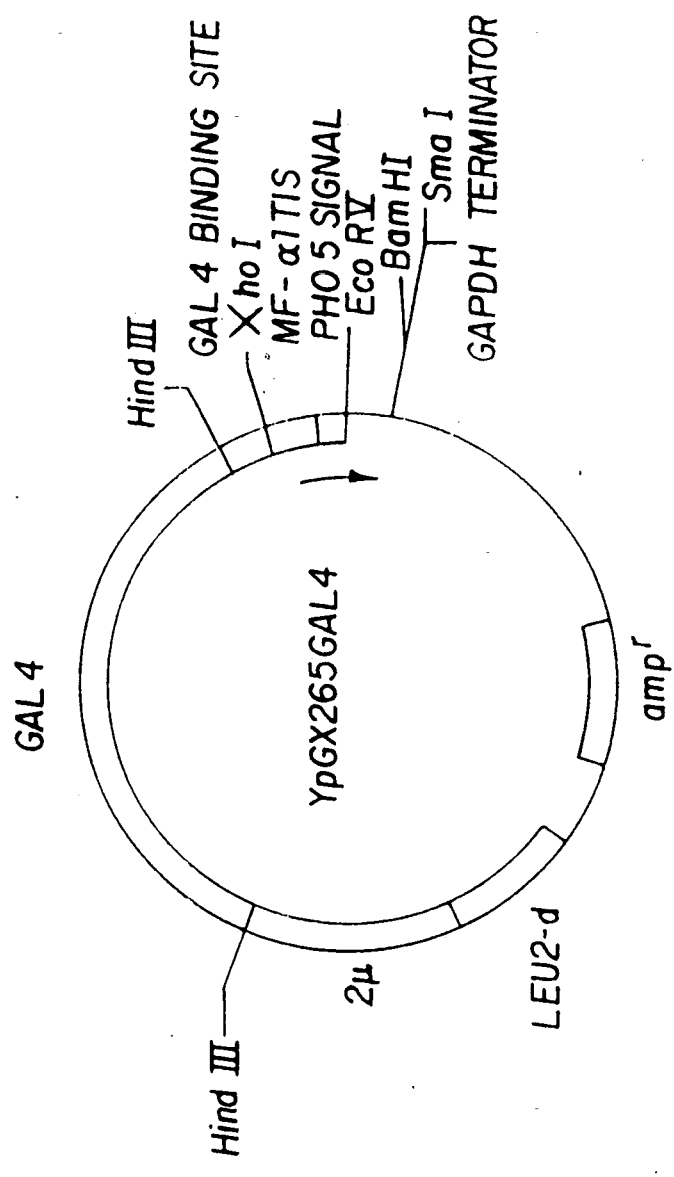
FIG. 8 is a restriction map of the YpGX265GAL4 . shuttle vector showing the position and orientation of the major functional elements, including the GAL4 binding site, the MF-alpha 1 transcription initiation site, the PH05 signal encoding sequence, the GAPDH terminator sequence, the *E. coli* ampicillin-resistance marker and the LEU2 marker for plasmid selection in *S. cerevisiae*. "TIS" is the abbreviation for transcriptional initiation site. The BamHI, EcorRV, XhoI, and SmaI sites are not unique in the plasmid.

The preparation of an expression vector of the invention generally involved the following series of steps:

(a) Isolating mRNA from the marine animal, e.g., from the phenol gland of the foot of *M. edulis*;

(b) Synthesizing complementary DNA (cDNA) and inserting the cDNA into bacteriophage;

(c) Transfecting *E. coli* with the recombinant bacteriophage and culturing the transfected *E. coli*;

(d) Selecting clones containing bioadhesive precursor protein genes by hybridization of transformants with a radiolabeled probe;

(e) Insertion of a DNA segment coding for a bioadhesive precursor protein into an expression vector as the 3' portion of a gene coding for a hybrid fusion protein. In some cases, a methionine residue is located on the amino terminal side of the amino acid sequence of the bioadhesive precursor protein. (By the term "DNA segment" is intended a portion, but less than the entirety, of the genome of the marine animal.)

The mRNA can be isolated from *M. edulis* by isolating the foot organ containing the phenol gland from live mussels; homogenizing the tissue in liquid nitrogen; dissolving the frozen tissue in guanidine thiocyanate as described by McCandliss, R. et al., *Methods Enzymol*, 79:51-57 (1981), or lysing the frozen tissue in the presence of ribonucleoside-vanadyl complexes and extracting the lysed tissue with phenol as described by Berger, S. et al., *J. Biol. Chem.*, 255:2955-2961 (1980); and purifying poly A-containing RNA by binding on oligo-dT cellulose as described by Aviv, H. and Leder, P., *Proc. Natl. Acad. Sci. U.S.A.*, 69:1408-1412 (1972). Similar procedures may be used in isolating the mRNA transcript of the gene of other marine animals encoding bioadhesive protein.

The mRNA extracted, i.e., from the phenol glands, is then employed as a template to produce cDNA in the presence of reverse transcriptase, dATP, dCTP, dGTP and dTTP, according to well-known procedures. Advantageously, a radioactive marker such as [alpha-$^{32}$P]dCTP is used to monitor the synthesis. The mRNA moiety is then removed using known procedures and a second strand of cDNA is synthesized, using the first strand as a template, in the presence of *E. coli* DNA polymerase I (Klenow fragment), dATP, dCTP, dGTP and dTTP. As those skilled in the art are aware, the double-stranded (ds-cDNA) DNA produced in this manner contains a hairpin loop. The single-stranded loop can conveniently be removed by digestion with S1 nuclease.

The ds-cDNA produced in the manner described is then inserted into a cloning vector in order to produce a library of clones to screen for the presence of the bioadhesive precursor protein gene. We employed the bacteriophage lambda gt10 as a cloning vector; however, those skilled in the art will be aware that any of numerous other vectors could conveniently be employed to the same end. In order to insert the dscDNA into the EcoRI site of lambda gt10, we first added synthetic 8-base pair EcoRI linkers to both ends of the ds-cDNA after blunting the ends of the ds-cDNA in the presence of DNA polymerase I (Klenow fragment) and dATP, dCTP, dGTP, and dTTP. To prevent cleavage of the ds-cDNA by EcoRI it was first methylated with EcoRI methylase. The linkers were phosphorylated in polynucleotide kinase buffer and ligated to the ends of the blunted ds-cDNA in the presence of T4 ligase. Multiple linkers were then removed from the ends by digestion with EcoRI. The ds-cDNA with EcoRI linkers was inserted into EcoRI-cut lambda gt10.

The cloning vector containing the cDNA is propagated in a suitable host. In the case of the recombinant lambda gt10, we packaged the recombinant phage DNA into bacteriophage lambda heads for introduction into *E. coli* strain BNN102 (Huynh, T.V. et al., Constructing and screening cDNA libraries in lambda gt10 and lambda gt11, In:D.M. Glover (ed.) DNA cloning, Vol. I, IRL Press, Oxford (1985), pp. 49-78) by procedures described by Enquist and Sternberg, *Methods Enzymol.*, 68:281-298 (1979). On this host strain, only lambda gt10 bacteriophage-carrying inserts at the EcoRI site will form plaques. The transfected hosts are cultured under appropriate conditions and examined for plaques.

The ds-cDNA library produced in the above manner is screened for the presence of the bioadhesive precursor protein gene by hybridization with a radiolabeled synthetic oligonucleotide probe. One predominant decapeptide in the bioadhesive precursor protein is known to be ala-lys-pro-ser-tyr-pro-pro-thr-tyr-lys. To screen the recombinant phage library for the precursor protein gene, we constructed and radiolabeled two 30-base synthetic oligonucleotide probes coding for the decapeptide, these two selected randomly from the 98,304 possible coding combinations. The two sequences selected were

GCG AAA CCA AGT TAC CCA CCG ACC TAC AAA and

GCG AAA CCT TCT TAT CCG CCT ACC TAT AAG.

Using hybridization washing conditions with decreased stringency that were previously established in Southern blot experiments and which are described in detail in the examples which follow, the radiolabeled probes were used to screen plaques which had been fixed on duplicate nitrocellulose filter replicates. To our knowledge, the 30-base probes are the shortest synthetic probes that have been used successfully in this type of screening. Plaques that gave positive signals by autoradiography of duplicate filters were purified, screened again and grown as plate lysates for DNA preparation as described in Maniatis, T. et al., "Molecular Cloning: A Laboratory Manual," Cold Spring Harbor Laboratory, pp. 371-372 (1982). The DNA sequence of the isolated clones can be determined by well-known methods.

Figure 1:
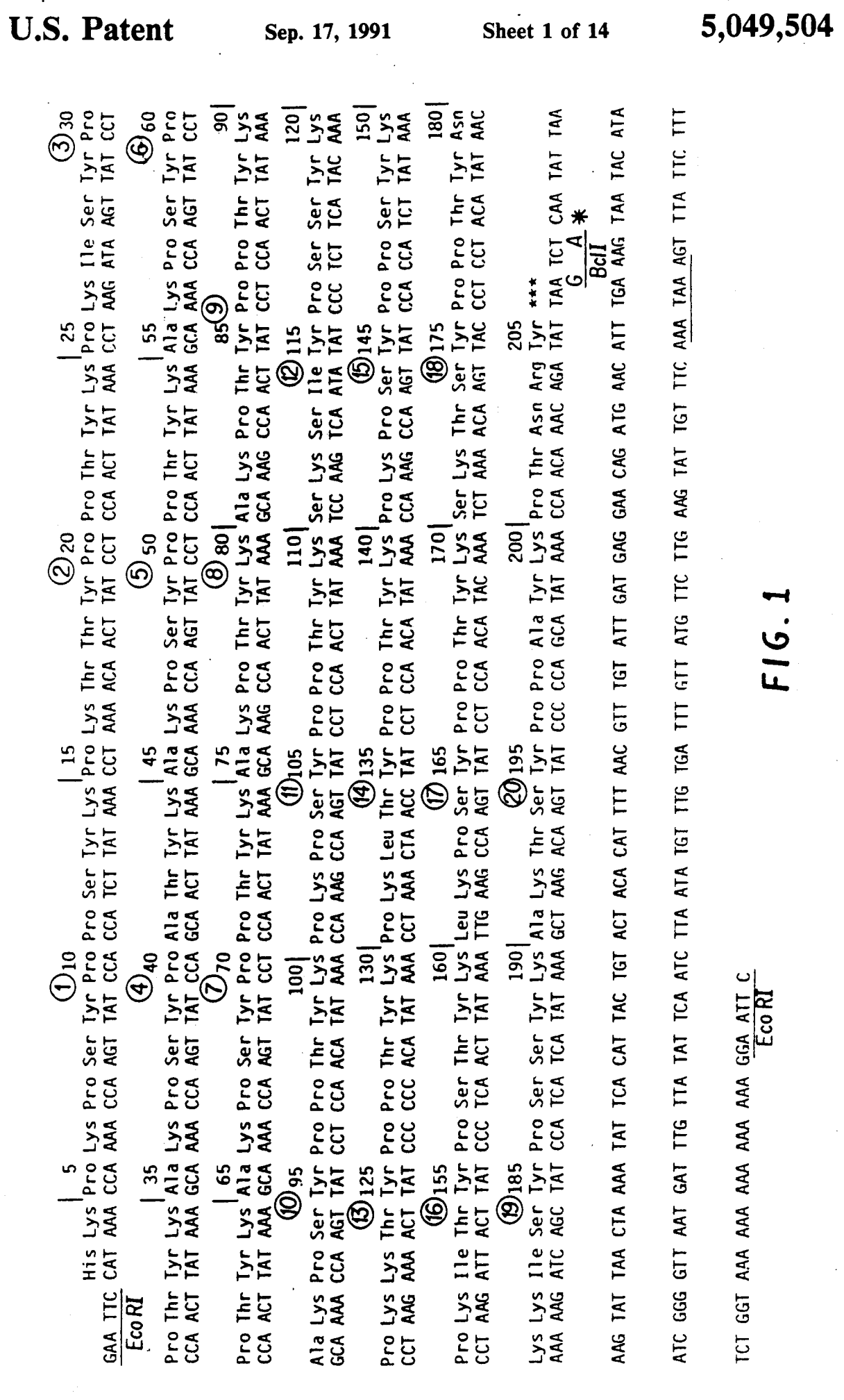

Using the procedures described generally above and described in greater detail in the examples that follow, we isolated several clones. Five have been characterized in detail and are identified herein as clones 14-1, 52, 55, 56, and N1, which contained DNA sequences coding for bioadhesive precursor proteins. FIG. 1 presents the DNA sequence and the translated amino acid sequence of the insert in clone 14-1. The DNA segment comprising the insert in clone 14-1 contains codons for a 203-amino acid sequence. In FIG. 1, the sequence has been divided to show 20 subunits, including 19 decapeptides and 1 hexapeptide (subunit no. 8).

FIG. 2 presents the DNA sequence and the translated amino acid sequence from the insert in cDNA clone 52. This DNA segment in the insert in cDNA clone 52 contains codons for a 334-amino acid sequence. In FIG. 2, the sequence has been divided to show 26 subunits which include 23 decapeptides and 3 hexapeptides, and an amino-terminal proline-rich segment. This cDNA clone and two of the other analyzed clones (55, 56) contain some noncoding DNA sequence (not shown) which we believe is derived from intron sequences. This suggests that some of the clones were derived from incompletely processed nuclear RNA.

The DNA sequences of the cDNA clones 14-1 and 52 display extensive homology at their 3'-ends. In particular, the last 138 codons of the translated regions are identical and include codons for a hexapeptide followed by 12 decapeptides (beginning at codon 75 of clone 14-1 in FIG. 1 and codon 205 of clone 52 in FIG. 2). Clone 52 contains a segment at the 5'-end that codes for a proline-rich segment of 82 amino acids. There is also a direct repeat of DNA sequences in clone 52. Specifically, the DNA for codons 92-147 is exactly repeated in codons 148-203

DNA sequences for cDNA clones 55 and 56 are shown in FIGS. 3 and 4. Codons 19-129 of cDNA clone 55 match the codons 148-259 of cDNA clone 52 with one exception. Codon 65 of clone 55 is an alanine while the clone 52 corresponding codon 195 is isoleucine.

There is also homology between the cDNA of clone 55 (FIG. 3) and the cDNA of clone 56 (FIG. 4) The codons 1-33 of clone 55 match codons 54-86 of clone 56. Some of the sequences are in the area where clone 55 also overlaps with clone 52, and in the direct repeating segment of clone 52.

The DNA sequence for clone N1 is shown in FIG. 9. Clone N1 does not have a perfect overlap with any of clones 14-1, 52, 55 or 56. Clone N1 also does not have a characteristic 5'-end sequence and therefore does not, in all likelihood, include the N-terminus of the natural gene. It does, however, code for a polypeptide with a molecular weight of about 80,000, a substantial portion of the natural polypeptide (molecule weight of 110,000-130,000).

Thus it can be seen that the cDNA clones are related in a complex way. Although there are areas in common, there is also generally divergence, suggesting either the existence of multiple genes or varied patterns of mRNA splicing for one gene or both.

As previously indicated, this invention provides expression vectors for microbial expression of bioadhesive precursor proteins. The expression vectors contain a DNA segment coding for a bioadhesive precursor protein such as that of a mussel of the genus Mytilus or a fragment thereof, the DNA segment being operably linked to a promoter and transcription initiation signals that are capable of effecting microbial expression. In one embodiment, the DNA segment contains codons for at least the portion of the amino acid sequence comprising subunits 8-20 of clone 14-1 and subunits 14-21 of clone 52; that is, amino acids 72-197 of clone 14-1 and amino acids 201-326 of clone 52.

FIGS. 6 and 7 outline one procedure that is employed to produce expression vectors of the invention. These expression vectors are capable of effecting expression of a bioadhesive precursor protein as a hybrid fusion protein which, in some cases, contains a methionine residue just upstream of the protein of interest. Since the bioadhesive precursor proteins encoded by all of the clones described above except clone N1 contain no methionine residues, they can be conveniently separated from the fused sequences by treatment with cyanogen bromide, which cleaves the fusion protein at methionine residues. As regards the protein encoded by the N1 clone, cyanogen bromide treatment may cleave at the methionine residue found in the second decapeptide, still leaving essentially the entire polypeptide intact. As the amino-terminal non-bioadhesive precursor protein amino acids will comprise at most roughly 15%, and in many cases much less, of the total adhesive protein precursor, removal of those amino acids by cyanogen bromide cleavage will not be necessary for all applications.

Referring to FIG. 6, the DNA segment containing the coding region for the bioadhesive precursor protein of clones 14-1 and 52 was obtained from the lambda gt10 cloning vectors by EcoRI digestion and subcloned into the EcoRI site of plasmid pGX2627. The resultant plasmids were designated pGX2368 and pGX2377.

Plasmids pGX2368 and pGX2377 were subjected to oligonucleotide-directed mutagenesis (Zoller, M.J. et al., *Methods Enzymol.*, Vol 100B, R. Woo, L. Grassa, and K. Moldave (eds.), Academic Press, New York, pp. 468-500 (1983)) to create BclI sites located at the translation terminators of each gene (see FIGS. 1 and 2). Since pGX2627 is a derivative of pGX1066 (ATCC No. 39955) that contains an M13 origin of replication, the pGX2368 and pGX2377 derivatives of pGX2627 were isolated in a single-stranded form for the oligonucleotide-directed mutagenesis experiments by infection of cultures with IR1 or M13 bacteriophage. The new plasmids containing BclI sites were designated pGX2380 and pGX2381.

The DNA segments containing the coding regions for the bioadhesive precursor proteins were then inserted into *E. coli* and yeast expression vectors in the proper reading frame. In an *E. coli* example presented below, the cDNA from phage 14-1 located in pGX2380 was cloned as a trpB gene fusion starting with an expression vector identified as pGX2287 that was designed for bovine chymosin production. Construction of this vector is described in detail in copending, commonly assigned U.S. Pat. No. 4,798,791. Plasmid pGX2287 has been deposited with the USDA Northern Regional Research Laboratory, Peoria, Ill., with accession No. NRRL-B15788. It contains the trpB bovine chymosin gene under the control of the leftward operator and rightward promoter regions of phage lambda (see copending, commonly assigned U.S. application Ser. No. 534,982) and an appropriately positioned transcription initiation signal. It also contains an ampicillin-resistance gene.

Plasmid pGX2287 was cut with ClaI, which cleaved the plasmid in trpB 24-base pairs upstream from the 5'-end of the chymosin coding sequence. A 116-base pair ClaI-SphI synthetic DNA was then ligated with linearized plasmid. The sequence of the synthetic DNA fragment which was ligated to the linearized plasmid is given in FIG. 5(b). The ligated DNA was then digested with SphI and the large fragment was isolated, resulting in the removal of a substantial portion of the chymosin coding region. The plasmid was then recircularized with T4 ligase. The resultant plasmid, identified pGX2346, contained the synthetic DNA fragment in place of the central portion of the chymosin gene.

Other specific vector constructions for the expression of the bioadhesive precursor protein will be apparent to those skilled in the art based on the description herein As a general rule, however, it is advantageous to construct the vector by inserting the bioadhesive precursor coding region as an in-frame fusion with another gene that is under the control of an efficient promoter. Preferably, the fusion is constructed such that the encoded fusion protein contains a methionine residue just upstream, e.g., within about 10 residues, from the bioadhesive precursor protein segment. In the specific construction described herein, pGX2383, there is a methionine residue 7 amino acids upstream from the bioadhesive precursor sequence. The recovered bioadhesive precursor protein can be treated with cyanogen bromide, using conditions well-known in the art, to remove extraneous amino acid sequences. As those skilled in the art are aware, cyanogen bromide cleaves proteins at methionine residues. Since there are no internal methionine residues within the bioadhesive precursor protein itself, the protein remains intact.

It will be readily apparent that modifications can be made in the vector construction such that the expression vector can carry the entire coding region for the bioadhesive precursor protein or a coding region for a fragment thereof. Preferably, the fragment contains at least about 5-20% of the coding sequence of a native bioadhesive precursor protein of a marine animal, e.g., of a mussel, e.g., of a mussel of the genus Mytilus. Encoded amino acids fused to the N-terminal or C-terminal ends of the encoded bioadhesive precursor, which cannot be removed by cyanogen bromide cleavage, are not believed to interfere with the functioning of the bioadhesive protein.

The expression vector provided by the invention is used to transform any suitable host microorganism, using known means, to produce a transformant. Suitable host organisms include, for example, *E. coli* or other related gram-negative organisms such as Salmonella, Klebsiella, Erwinia, etc. With plasmids related to pGX2383 the host preferably contains the lambda cI857 gene coding for temperature-sensitive lambda repressor. In the case of pGX2383, we chose to employ E. coli strain GX3015 as the host. This was because pGX2383 contains the trpED portion deleted in the trpED102 chromosomal deletion in GX3015. The plasmid is therefore stabilized by growing the transformant in a tryptophan-deficient medium.

In a different embodiment, an expression vector may be used to transform yeast, e.g., *Saccharomyces cerevisiae*. Typical vectors of this type are disclosed in U.S. application Ser. No. 918,147, filed on Oct. 14, 1986, and having the title "Composite Yeast Vectors," incorporated by reference herein. One preferred vector for expression of bioadhesive precursor protein in yeast comprises the yeast shuttle vector YpGX265GAL4 (ATCC #67233). This vector is characterized by a promoter that is a hybrid-derived from the *S. cerevisiae* GAL1 and MF-alpha 1(alpha-factor) promoters. This promoter system permits galactose-regulated expression. The regulatory gene comprises the GAL4 gene which encodes GAL4 protein, a positive regulator of the GAL1-MF-alpha 1 hybrid promoter derived from *S. cerevisiae*. The terminator in the YpGX265GAL4 vector system is derived from synthetic DNA and is based on *S. cerevisiae* GAPDH transcription terminator. The signal encoding sequence, also derived from synthetic DNA, is based on the *S. cerevisiae* PH05 signal. Codons are designed substantially for usage preference in *S. cerevisiae*.

The YpGX265GAL4 vector contains the LEU2 gene, a marker for plasmid selection in *S. cerevisiae*. It also contains DNA derived from *S. cerevisiae* 2-micron plasmid which provides a plasmid replication origin for *S. cerevisiae*. The vector is further characterized by the *E. coli* replication origin derived from pAT153, and *E. coli* selectable marker which is ampicillin resistance, also derived from pAT153. The heterologous gene (the gene coding for bioadhesive precursor protein) is inserted between the PHO5 signal-encoding sequence and the GAPDH terminator.

A typical shuttle vector preparation is as follows. YpGX265GAL4 is digested with restriction endonuclease HindIII and large and small DNA fragments are gel-purified. The larger fragment is digested with restriction endonuclease SmaI, generating two DNA fragments. M13mp9 (commercially available) is digested with SmaI and HindIII and treated with calf alkaline phosphatase. The DNA fragments reated by the SmaI digestion of the larger HindIII fragment of YpGX265GAL4 and from digestion of the M13mp9 are ligated and used for transformation of *E. coli*. The transformants containing phage double-stranded DNA with the yeast promoter-terminator cassette are identified, digested with restriction endonucleases (EcoRV and BamHI) and the large fragment (approximately 8 kilobase) is gel-purified. A plasmid containing bioadhesive precursor protein cDNA (i.e., pGX2380) is digested with restriction endonuclease LbaI, and the single-stranded overhang is filled with the Klenow fragment of DNA polymerase. The DNA molecule resulting from the XbaI and DNA polymerase treatment of pGX2380 is digested with BclI. The resulting approximately 625-bp DNA fragment is gel-purified. Oligonucleotide linker sequences are annealed and used in a three-way ligation with the DNA fragments created by restriction of the phage double-stranded DNA and the cDNA-derived DNA molecule with the modified XbaI and BclI end.

*E. coli* transformants containing the desired phage DNA molecules are identified by restriction endonuclease digestion. This phage DNA may be digested with restriction endonucleases (SmaI and HindIII), with the small (approximately 1,300 base pair) fragment gel-purified. YpGX265GAL4 is digested with SmaI and HindIII and the large fragment is gel-purified. The DNA molecules created by the SmaI-HindIII digestions are ligated and used to transform E. coli. The desired plasmid may be linearized with restriction endonuclease (HindIII) and treated with calf alkaline phosphatase. The 3.65-kb GAL4-containing fragment obtained from the original restriction digestion may by ligated with the linearized DNA and used to transform *E. coli*.

Saccharomyces strains carrying mutations in the LEU2 structural gene (e.g., AH22 (ATCC #38626)) may be transformed with this plasmid, utilizing standard methods. The yeast strain may be grown in an appropriate medium (YNBD, containing 0.7% yeast nitrogen base, 2% glucose, 20 mg/liter L-histidine) to maintain the plasmid.

While the above typifies one construction technique for yeast expression, it is readily apparent that one with ordinary skill can impart modifications and variations within the general teaching. As with the vectors described above, the expression vector may comprise the entire coding region for the bioadhesive precursor protein or coding regions for fragments thereof.

For production of the bioadhesive precursor protein, the transformed yeast strain may be grown in an appropriate medium. One suitable medium contains 1% yeast extract, 2% peptone, 1% glucose, and 1% galactose.

The transformant microorganism is cultured under conditions suitable for growth and expression of the bioadhesive precursor protein gene. After the protein has been expressed, it is recovered from the transformant by known methods such as by mechanical or chemical lysis of the cells. The protein can be purified using procedures known in the art, including well-known chromatographic procedures. The bioadhesive precursor protein is preferably purified to homogeneity or near homogeneity. In the case of a fusion protein such as that expressed by pGX2383, the recovered protein can be subjected to cyanogen bromide cleavage to remove extraneous peptide sequences.

The recovered bioadhesive precursor protein is converted to a bioadhesive by hydroxylation. In particular, it is likely to be necessary to hydroxylate at least a portion of the tyrosine or tyrosine and proline residues, an event that occurs in vivo in the mussel. Hydroxylation converts tyrosine residues to DOPA residues and, optionally, proline residues to hydroxy proline residues. The DOPA hydroxyl groups are believed to displace water at the bond surfaces, thus contributing to the excellent wet strength of the adhesive, and DOPA residues oxidized to quinones participate in intermolecular cross-linking which cures the adhesive and imparts cohesivity.

Any suitable chemical or enzymatic means for effecting hydroxylation can be employed. It is preferred, however, to effect hydroxylation enzymatically using an enzyme such as mushroom tyrosinase or *Streptomyces antibioticus* tyrosinase. Enzymatic hydroxylation procedures using these enzymes are carried out as generally described by Ito et al., *Biochem. J.* 222: 407–411 (1984) and Marumo and Waite, *Biochem. Biophys. Acta* 872:98–103 (1986). Preferably, at least about 10% of the tyrosine residues are hydroxylated. The mushroom tyrosinase is removed from the protein using known procedures such as binding to a LH-Sephadex 60 column followed by elution with 0.2 M acetic acid or by membrane filtration. The bioadhesive protein can be lyophilized for reconstitution as an adhesive formulation at a later date.

The bioadhesive protein can be employed in the form of a solution in a suitable solvent with or without other adhesive substances. Suitable solvents for the bioadhesive include water or aqueous solutions of alcohols such as methanol, ethanol, propanol, and the like, acetone, DMSO, dimethyl formamide, and the like.

The concentration of bioadhesive protein in the solution can range from very low to very high, depending upon the intended application.

The bioadhesive protein or a solution or formulation containing the bioadhesive protein can be employed as a primer, i.e., a preadhesive film or coating to improve the total adhesive bond to a surface. It may also be employed as a component in an adhesive system to impart or improve water-resistant adhesivity. Another use within the scope of the invention includes use as a thin film membrane, or as a component in a thin film or membrane, particularly to impart desirable permeability characteristics and/or moisture resistance to such film or membrane. Yet another use is as a sealant or component of a sealant to prevent moisture penetration.

A solution of the bioadhesive protein can be uniformly coated on a surface as a primer. Curing of the primer coating occurs in a normal air environment by cross-linking, which may be indicated by the development of a brown or tan color when used in high concentration. A conventional adhesive such as an epoxy adhesive is then applied over the primer coat and the surfaces to be bonded are brought together.

In another embodiment of the invention, an adhesive composition is provided that contains the hydroxylated bioadhesive protein in solution with another adhesive substance. Typical of the adhesives that may be employed in conjunction with the bioadhesive protein of the invention are the carbohydrate adhesives and the synthetic resin adhesives such as the polyacrylates, polyepoxides, resols, etc. The known carbohydrate adhesives that can be employed include chitosan, starch, pectin, glucan, dextran, etc.

A preferred carbohydrate adhesive is chitosan purified from crab or shrimp shell chitin by the procedure of Skujins, J. J. et al., *Arch. Biochem. Biophys.*, 111:359 (1965). The free amino groups of chitosan are reactive with the DOPA-derived quinones of oxidized bioadhesive protein, providing covalent cross-links between the two polymers. Chitosan at appropriate concentrations provides bioadhesive protein mixtures with a high viscosity and excellent adhesive strength. The high viscosity is a particularly useful property in underwater applications where diffusion can cause a loss of material before the adhesive has an opportunity to cure.

A preferred adhesive mixture comprises from 0.1% to 30% of the hyroxylated bioadhesive polymer and from 1% to 7% chitosan, the balance being solvent. The pH of the composition is from about 5.5 to 7.0. The composition can be cured at pH 6.0 by the addition of catechol oxidase or tyrosinase which catalyzes the formation of DOPA-derived quinones and cross-linking.

In another embodiment of the invention, there is provided an adhesive composition in which the bioadhesive protein is admixed with other proteins that improve its physical properties such as cohesivity. A preferred protein for this protein is collagen. A preferred composition comprises a solution having 0.1% to 70% solids, the solids in the solution comprising from 1% to 50% bioadhesive protein and from 50% to 99% collagen.

The bioadhesive protein of the invention, with or without the addition of other proteins, is particularly useful as a biomedical adhesive or sealant in a variety of medical applications, for example, in wound healing. Being a biological material, the bioadhesive protein presents a greatly reduced risk of toxic degradation products as compared with a synthetic adhesive. The bioadhesive protein can be applied as a biomedical sealant in much the same manner as fibrin (see e.g., Redl, A. and Schlag, C., *Facial Plastic Surgery*, 24:315-321 (1985)).

The following examples are intended to illustrate further the practice of the invention and are not intended to limit its scope in any way.

EXAMPLE 1

Production of Antibody to Bioadhesive Precursor Protein

Synthetic decapeptide (1.5 mg) with the predominant sequence of *M. edulis* bioadhesive precursor protein (ala-lys-pro-ser-tyr-pro-pro-thr-tyr-lys) prepared by the Merrifield solid state method was combined with 2.0 mg of bovine serum albumin (BSA) in 1.8 ml phosphate-buffered saline. One percent glutaraldehyde (0.2 ml) was added and the solution was incubated 30 minutes at 22° C. Sodium borohydride was added to a final concentration of 0.5 mg/ml and incubation was continued at 22° C. for one hour. The solution was then dialyzed against phosphate-buffered saline. Amino acid analysis of the resulting protein indicated 35 moles of peptide were coupled per mole of BSA.

Rabbits were given intramuscular injections with 100 ug of peptide (BSA coupled) incomplete Freund's adjuvant. Booster subcutaneous injections using incomplete Freund's adjuvant were given subsequently in two-week intervals. Antiserum with high-titer antibody reactive toward the decapeptide as well as *M. edulis* bioadhesive precursor protein isolated from mussels or produced in microorganisms was obtained by this method.

EXAMPLE 2

Isolation of *M. edulis* Bioadhesive Precursor Protein mRNA

The adductor muscles of live blue mussels (*Mytilus edulis*) were cut and the foot organ containing the phenol gland was amputated, quickly cut in small pieces and frozen in liquid nitrogen. The frozen tissue was shattered into small pieces by mixing in liquid nitrogen at top speed in a commercial Waring blender with a metal container. The pulverized tissue was stored at −80° C. until use.

The frozen tissue was dissolved in a 4 M guanidine thiocyanate solution as the first step in the RNA isolation procedure (McCandliss, R. et al., *Methods Enzymol*, 79:51-59 (1981)). From 22.1 g wet weight of tissue, 28.3 mg of total RNA was obtained. Poly A-containing RNA was purified by selecting the RNA that would bind to oligo-dT cellulose (Aviv, H. and P. Leder, *Proc. Natl. Acad. Sci. U.S.A.* 69:1408-1412 (1972)). Two oligo-dT cellulose selections yielded 0.6% of the total RNA (approximately 170 ug) that included polyadenylated mRNA.

As an alternative to the guanidine isolation procedure, a modification of the procedure of Berger, S. et al., *J. Biol. Chem.*, 255:2955-2961 (1980) was used. Five grams of the frozen mussel tissue above after lyophilization were suspended in 100 ml of 10 mM Tris-HCl, pH7.5, 10 mM NaCl, 1.5 mM $MgCl_2$, 0.2% NP-40, and 10 mM ribonucleoside-vanadyl complexes (VRC, Bethesda Research Laboratories), 100 ml of phenol were added, and the solution was mixed at top speed in a Virtis homogenizer for 2 min. The suspension was centrifuged to separate the phases and the aqueous phase was removed. The organic phase was extracted with 50 ml of 0.2M sodium acetate, pH5.5, and the aqueous phase was combined with the phase earlier recovered. The aqueous phases were extracted three times with phenol containing 0.1% 8-quinolinol. The RNA (with some genomic DNA) was precipitated with ethanol. Poly A-containing RNA was purified as above. From 5 g of tissue, approximately 150 ug of poly A RNA were isolated.

EXAMPLE 3

Synthesis and Cloning of *M. edulis* cDNA Stock Solutions and Materials for First Strand cDNA Synthesis 0.5 M Tris-HCl, pH 8.3
0.25 M $MgCl_2$
0.05 M dATP, pH 7.0

0.05 M dGTP, pH 7.0
0.05 M dCTP, pH 7.0
0.05 M dTTP, pH 7.0
[alpha-$^{32}$P]dCTP, 400 Ci/mmol, 1 mCi/ml (Amersham), stabilized aqueous solution
0.1 M dithiothreitol (DTT)
Oligo (dT)$_{12-18}$ 1,000 ug/ml (Collaborative Research, Waltham, Mass.)
0.1 M sodium pyrophosphate
0.2 M disodium ethylenediaminetetraacetate (EDTA), pH 8.0
RNasin, ribonuclease inhibitor 30 units/ul, (Promega Biotec)
Avian myeloblastosis virus (AMV) reverse transcriptase, approximately 10,000 units/ml (obtained from Life Sciences, Inc., St. Petersburg, Fl.)

All buffers and salt solutions were autoclaved. The other solutions were prepared with sterile glassdistilled water and were stored in sterile containers. All stock solutions were stored frozen. All enzymes were obtained commercially and used according to the manufacturer's specifications unless otherwise noted.

As a template for cDNA synthesis, mRNA prepared by the guanidine method described in Example 2 was employed. In order to follow the synthesis, a radioactive marker ([alpha-$^{32}$P]dCTP) was used. This allows monitoring of all steps by counting Cerenkov radiation, which does not result in any loss of sample. For each ug of mRNA, 2 uCi of [alpha-$^{32}$P]dCTP at a specific activity of 400 Ci/mmol were used The radioactive material was added to a 2× reaction mixture consisting of 0.1 M Tris-HCl, pH 8.3, 20 mM MgCl$_2$, 1 mM dATP, 1 mM dCTP, 1 mM dGTP, 1 mM TTP, 20 mM DDT, and 5mM sodium pyrophosphate. This solution was kept on ice. To this solution was added mRNA (50 ug/ml, final concentration), oligo (dT)$_{12-18}$ (100 ug/ml), RNasin (600 units/ml), AMV reverse transcriptase (800 units/ml), and enough water to dilute the 2× mix to 1×. After 5 minutes on ice, the reaction mixture was incubated at 46° C. for 10 minutes. Following the incubation, EDTA was added to a final concentration of 25 mM. The solution was extracted one time with an equal volume of phenol:chloroform (1/1; v/v) and the aqueous phase was chromatographed on a column of Sephadex G-100 (0.7×20cm) equilibrated with 10 mM Tris-HCl, pH 8.0, 1 mM EDTA, 0.1 M NaCl. The mRNA:cDNA hybrid in the excluded volume was precipitated by addition of 0.1 volume of 3 M sodium acetate and 2 volumes of 95% ethanol (−20° C. to −80° C.) In order to remove the mRNA moiety, the pelleted hybrid was dissolved in 300 ul 0.1 M NaOH and incubated at 70° C. for 20 minutes. The solution was cooled on ice and neutralized with 30 ul of 1N HCl. The cDNA was precipitated as described above.

Stock Solutions and Materials for Second Strand cDNA Synthesis 0.5 M potassium phosphate, pH 7.4
0 25 M MgCl$_2$
0 1 M Dithiothreitol (DTT)
0.05 M dATP, pH 7.0
0.05 M dGTP, pH 7.0
0.05 M dCTP, pH 7.0
0.05 M dTTP, pH 7.0
E. coli DNA polymerase I (Klenow fragment), approximately 5,000 units/ml (Boehringer-Mannheim)

10× S1 nuclease buffer 0.5 M sodium acetate, pH 4.5; 10mM ZnSO$_4$, 2 M NaCl, 5% glycerol It was not necessary to use a radioactive label in the second strand, since the first strand was labeled. A 2× reaction mixture consisting of 0.2 M potassium phosphate, pH 7.4, 20 mM MgCl$_2$, 2 mM DTT, 0.4 mM each of dATP, dGTP, dCTP, and dTTP was prepared and kept on ice. To this mixture was added an aqueous solution of cDNA containing the Klenow fragment of E. coli DNA polymerase I (100 units/ml, final concentration), and water was added to dilute the reaction mixture to 1X. The solution was incubated overnight at 15° C. After the incubation, EDTA was added to 25 mM, the solution was extracted once with an equal volume of phenol: chloroform (1/1; v/v), and the aqueous phase was chromatographed on a 0.7×20 cm column of Sephadex G-100 equilibrated with 10 mM Tris-HCl, pH 8.0, 1 mM EDTA, and 0.1 M NaCl. The DNA in the excluded fractions was precipitated with ethanol as described above.

At this point, the ds-cDNA was in the form of a hairpin. The single-stranded loop was removed by digestion with S1 nuclease The ds-cDNA was dissolved in water and 0.1 volume of 10× S1 buffer was added. An appropriate amount of S1 nuclease was added and the solution was incubated 20 minutes at 37° C. The amount of enzyme added was determined empirically for each enzyme preparation, since the activity varied from one preparation to another. This was done by measuring the decrease in TCA-precipitable counts from the dscDNA. Generally, a decrease of 20–40% was observed. The S1-digested cDNA was extracted once with phenol: chloroform and the cDNA in the aqueous phase was precipitated with ethanol as described above.

Addition of Linkers to cDNA

For insertion of the cDNA into the EcoRI site of lambda gt10 vector, EcoRI linkers were added to the ends of cDNA molecules. To prevent cleavage of internal EcoRI sites in the cDNA molecules with EcoRI, the cDNA was first methylated with EcoRI methylase.

Stock Solutions and Materials

5×EcoRI methylase buffer—0.5 M Tris-HCl, pH 8.0, 0.05 M EDTA.
8 mM S-adenosyl methionine (SAM)—solution in 0.01 M H, pH 2, 10% ethanol.
1 mg/ml bovine serum albumin (BSA)—solution in water, sterile filtered.
8-base pair EcoRI linkers—10 A$_{260}$/ml, obtained from Collaborative Research, Waltham, Mass.
10 mM ATP, pH 7.0
10×T4 polynucleotide kinase buffer—0.7 M Tris-HCl, pH 7.6, 0.1 M MgCl$_2$, 50 mM dithiothreitol.
gamma[$^{32}$P]-ATP—10 mCi/ml, 2,000 Ci/mmol, stabilized aqueous solution.
10×T4 ligase buffer—0.5 M Tris-HCl, pH 7.8, 0.1 M MgCl$_2$, 0.2 M dithiothreitol.
10×DNA polymerase buffer—0.5 M Tris-HCl, pH 7.2, 0.1 M MgSO$_4$.
2 mM dATP, dCTP, dGTP, dTTP mixture, pH 7.0.
1 mM dithiothreitol
10×EcoRI buffer—1.0 M Tris-HCl, pH 7.5, 0.5 M NaCl, 0.05 M MgCl$_2$.

The cDNA fragment produced as described above was dissolved in 20 ul of 5×EcoRI methylase buffer, SAM was added to 80 uM, BSA was added to 0.4 mg/ml, water was added to bring the volume to 99 ul, and 1 ul of EcoRI methylase (20,000 units/ml, New England Biolabs) was added. The reaction was incubated at 37° C. for 60 minutes. The reaction was then extracted 2 times with phenol and ethanol-precipitated. The methylated cDNA was collected by centrifugation and dried.

Before addition of the linkers, the cDNA was treated with DNA polymerase I (Klenow fragment) in the presence of deoxynucleoside triphosphates to make the ends of the cDNA blunt. The cDNA was dissolved in 24 ul of 1× DNA polymerase buffer containing 80 uM each dATP, dCTP, dGTP and dTTP. Two units of DNA polymerase (Klenow fragment) were added and the reaction mixture was incubated at 23° C. for 10 minutes. EDTA was added to 20 mM and the cDNA was extracted two times with phenol, once with $CHCl_3$, and ethanol-precipitated. The cDNA, which was EcoRI-methylated and blunt-ended, was collected by centrifugation, washed once with cold 70% ethanol, and dried.

To prepare the linkers for addition to the cDNA, the linkers first had to be phosphorylated. 400 Picomoles of 8-base pair EcoRI linkers were phosphorylated in 1× polynucleotide kinase buffer with 20 uCi of [qamma-$^{32}$P]-ATP and 5 units of polynucleotide kinase. The reaction was incubated at 37° C. for 15 minutes. Unlabeled ATP was then added to 1 mM and the reaction was incubated at 37° C. for 30 minutes. The enzyme was inactivated by heating the reaction at 65° C. for 10 minutes. 160 picomoles of the phosphorylated linkers were then ligated to the cDNA. The blunt-ended, methylated cDNA was dissolved in 10 ul of water, 160 picomoles of linkers were added, 10×T4 ligase buffer was added to 1×, ATP was added to 1 mM, and 2 units of T4-DNA ligase (Boehringer-Mannheim) were added. The reaction mixture (a total of 20 ul) was incubated at 15° C. for 16 hours. The ligase was inactivated by heating the reaction of 65° C. for 10 minutes.

At this point, the cDNA had multiple linkers at the ends. Excess linkers were removed by digestion with EcoR1.

The ligation reaction was diluted with 5 ul of 10×EcoR1 buffer, 5 ul of 1 mg/ml BSA and 19 ul of water. Prior to addition of EcoRl, 1 ul of the mix was removed for analysis by gel electrophoresis. Ten units of EcoR1 (New England Biolabs., 10 units/ul) were added and the reaction was incubated at 37° C. for 1 hour. The reaction was extracted 1 time with phenol and run over a column of Sephadex G-100 equilibrated with 10 mM Tris-HCl, pH 8.0, 1 mM EDTA, and 0.1 M NaCl. The DNA in the excluded fractions was concentrated by use of a Centricon 30 microconcentration unit (Amicon) according to manufacturer's instructions. The cDNA was loaded on 5-25% sucrose gradient in 50 mM Tris-HCl, pH 8.0, 1 mM EDTA and the gradients were centrifuged at 5° C. at 38,000 r.p.m. for 17 hours in a Beckman SW41 rotor. Fractions were collected and were analyzed by counting Cerenkov radiation. Parallel gradients were run with molecular weight markers Fractions containing cDNA of approximately 1,000- base pairs and longer were pooled and the cDNA was concentrated with a Centricon 30 microconcentration unit. The cDNA was washed four times with 1 ml of $H_2O$ to remove the sucrose and was dried in vacuo.

Preparation of Recombinant Bacteriophage DNA

Bacteriophage lambda gt10 DNA (Huynh, T.V. et al., Constructing and screening cDNA libraries in lambda gt10 and lambda gt11, In: D.M. Glover (ed.) DNA cloning, Vol. 1, IRL Press Oxford 1985, pp. 49-78) prepared by standard methods (Maniatis, et al., *Molecular Cloning*, Cold Spring Harbor, 1982) was linearized by digestion with EcoRI, phenol-extracted, and precipitated with ethanol. Fifty ng cDNA were mixed with 1 ug EcoRI-cut lambda gt10 (a molar ratio of approximately 2:1) in 50 mM Tris-HCl, pH 7, 10 mM $MgCl_2$, 20 mM dithiothreitol, and 1 mM ATP, and 1 unit of T4DNA ligase (Boehringer-Mannheim) was added. The ligation mixture was incubated for 16 hours at 15° C. A small portion of the reaction mix was analyzed by agarose gel electrophoresis. The desired product at this point was high molecular weight, concatameric DNA, which was in the form required for efficient packaging into empty bacteriophage lambda heads.

Packaging of the Recombinant DNA into Bacteriophage Lambda Heads and Transfection into *E. coli*

The recombinant DNA was packaged into bacteriophage lambda heads for introduction into *E. coli*, by procedures described by Enquist and Sternberg, *Methods Enzymol.*, 68:281-298 (1979). Packaging extracts are available commercially (Promega Biotec, Madison, Wisconsin, and other sources) and were used according to the manufacturer's instructions. The ligated DNA was mixed with the packaging extracts (50 ul), incubated at 23° C. for 2 hours; the phages were diluted with 0.5 ml, 10 mM $MgSO_4$, 10 mM Tris-HCl, pH 7.5, 0.01% gelatin, and a few drops of chloroform were added to the mixture. The packaged phages were stored at 4° C.

As a host for titration and propagation of the phage, *E. coli* strain BNN102 (Huynh, T.V. et al., supra) was used. On this host strain, only lambda gt10 bacteriophages carrying inserts at the EcoRI site will form plaques. The host strain was grown overnight at 37° C. in LB-broth containing 0.2% maltose, to induce synthesis of the phage receptor in the host. The cells were collected by centrifugation and resuspended in one-half volume of 10 mM $MgSO_4$. Cells prepared in this manner were used for 1-2 days.

The phage were diluted serially in 10 mM $MgSO_4$, 10 mM Tris-HCl, pH 7.5, and 0.01% gelatin. Fifty ul of diluted phage were added to 0.2 ml of *E. coli* cells, and the mixture was incubated at 37° C. for 15 minutes to allow absorption of the phage. The infected cells were mixed with molten (47° C.) LB broth containing 0.7% agar and poured on the LB-agar plate After the top agar hardened, the plates were incubated at 37° C. for 5-6 hours, at which time plaques could clearly be seen in the lawn of bacteria. A library of approximately 500,000 recombinant phages was obtained.

EXAMPLE 4

Selection of Bioadhesive Precursor Protein cDNA Clones from the *M. edulis* cDNA Phage Library The lambda gt10 phage library was plated on twenty 15-cm petri dishes at a density of approximately 25,000 phage/plate. Duplicate nitrocellulose filter replicates were prepared for hybridization screening (Benton, W.D. and R.W. Davis, *Science* 196:180 (1977)). Two 30-base synthetic oligonucleotides (GCG AAA CCA AGT TAC CCA CCG ACC TAC AAA and GCG AAA CCT TCT TAT CCG CCT ACC TAT AAG) were prepared with an Applied Biosystems DNA synthesizer. These sequences are two of the possible 98,304 coding sequences for the predominant decapeptide (ala-lys-pro-ser-tyr-pro-pro-thr-tyr-lys) of *M. edulis* bioadhesive precursor protein. The oligonucleotides were radioactively labeled to a specific activity of approximately $10^8$ cpm/ug with gamma-[$^{32}$P]-ATP (New England Nuclear) and T4 polynucleotide kinase (Boehringer-Mannheim), then used as hybridization probes. The radioactive oligonucleotides (approximately 3.0 ug) were added to 250 ml hybridization solution containing 20% formamide, 6XSSC, 5× Denhardt's solution, 50 mM phosphate buffer (pH 6.8), 100 ug/ml sonicated denatured salmon sperm DNA and 10% dextran sulfate. The filters were hybridized for 14 hours at 30° C., then washed five times briefly with 300 ml 6XSSC at 22° C., one time with 300 ml 1XSSC at 22° C. and once at 42° C. for 30 minutes with 500 ml 1XSSC. The filters were air-dried and autoradiographed at −80° C. with Kodak XAR X-ray film for 12 hours These hybridization and washing conditions were previously established in hybridization to *M. edulis* DNA with the same probe on Southern blots (Southern, E, *J. Mol Biol.*, 98:503 (1976)). A 42° C. wash in 1XSSC was the highest temperature that demonstrated apparently specific hybridization to a fragment of BamHI-digested *M. edulis* DNA. The DNA for the Southern blot experiment was isolated from the frozen tissue described in Example 2 by the method of Blin and Stafford (Blin, N. and D.W. Stafford, *Nuc. Acids Res.*, 3:2303–2308 (1976)).

Plaques giving signals by autoradiography on the duplicate filters were purified by picking, diluting, plating and repeating the hybridization screen described above. Isolated individual plaques giving radioactive signals were picked and grown as plate lysates for DNA preparation as described (Maniatis, T. et al., "Molecular Cloning: A Laboratory Manual," Cold Spring Harbor Laboratory, 1982, pp. 371–372).

EXAMPLE 5

DNA Sequence Analysis to Verify Clones

DNA from lambda gt10 clone 14-1 and other clones with putative bioadhesive precursor protein cDNA inserts were digested with restriction endonuclease EcoRI. The EcoRI cDNA fragment was cloned into M13 mp11 (Norrander, J et al. *Gene*, 26:101–106 (1983)). The bacteriophage M13 derivatives were constructed using methods described by Messing (Messing, J., *Methods Enzymol.*, 101:20–78 (1983)). Both orientations of the inserts were represented in independent clones. Some of the larger inserts were progressively shortened by the procedure of Dale et al. (*Plasmid*, 13:31–40 (1985)). The phage clones were sequenced by the dideoxy method (Biggin, M.D. et al., *Proc. Natl. Acad. Sci. U.S.A.*, 80:3963–3965 (1983)). The recorded DNA sequences were analyzed with VAX 780 computer assistance. The DNA sequence and translated amino acid sequence of clone 14-1 are presented in FIG. 1. Clone 14-1 encodes a polypeptide with tandem repeats of 19 decapeptides and 1 hexapeptide. Clone 52, presented in FIG. 2, encodes a polypeptide with a mix of 22 decapeptide repeats and 4 hexapeptide repeats preceded by an 82-amino acid segment that is proline rich. Proline-rich segments such as this had not been previously described in *M. edulis* polyphenolic protein. Clones 14-1 and 52 share considerable homology in their 3'-ends. After a short untranslated trailer sequence in both clones, there is the polyadenylation signal AATAAA located just prior to a stretch of A residues These features are expected at the authentic 3'-terminus of mRNA.

EXAMPLE 6

Isolation of Full-Length *M. edulis* Bioadhesive Precursor Protein cDNA

A. mRNA isolation

The partial bioadhesive precursor protein cDNAs shown in FIGS. 1–4 that were isolated and characterized as described in Examples 1–5 are used to isolate full-length bioadhesive precursor protein cDNA This is accomplished through use of the initial clones as hybridization probes of more carefully prepared cDNA clone banks.

The mRNA used in Example 3 was prepared from mussels obtained in a grocery store that were not actively producing byssus threads and adhesive plaques. This may have resulted in low-level and poor quality adhesive protein mRNA. In order to obtain mRNA of better quality, fresh mussels were obtained directly by air freight delivery from the Blue Gold Sea Farms in Rhode Island. The mussels had no treatment after harvesting other than tumbling to clean their outer shells. The mussels were introduced into a 20-gallon aquarium tank placed in a 4° C. room with 10 gallons of synthetic sea water (Instant Ocean, Aquarium Systems, Mentor, Ohio) heated to approximately 12°–15° C. The tank water was mixed and the temperature regulated with a Precision H7B heater. Additional rapid agitation was provided by a lighting series 30 mixer (Mixing Equipment, Co., Inc., Rochester, N.Y. 14603). When individual mussels became active in attachment, they were removed and the distal end of the foot was quickly amputated and immediately frozen by dropping into liquid nitrogen. The tissue was ground into a powder by mixing in liquid nitrogen in a Waring blender, and then lyophilized. The mRNA was isolated by the procedure using ribonucleoside-vanadyl complexes as described in Example 2.

B. cDNA Synthesis and cDNA Clone Selection

The mRNA is used to synthesize cDNA as described in Example 3. However, this time when the double-stranded cDNA is fractionated on a 5–25% sucrose gradient, a much more stringent size selection is used where only cDNA of approximately 3,000 base pairs or larger is pooled for cloning.

The phage library and screening is carried out as described in Examples 3 and 4, except that the EcoRI insert fragment of clone 14-1 is isolated and made radioactive by nick translation (Rigby, P.W.J. et al, *J. Molec. Biol.* 113:237) with [alpha-32P]-dCTP label Hybridization is carried out at 42° C. in 6XSSC, 50% formamide, with 5×Denhardt's solution and 100 ug/ml denatured salmon sperm DNA. The filters are washed at 50° C. with 0.1×SSC with 0.1% SDS. Hybridi-zation-positive plaques identified in duplicate are purified and DNA is prepared as described in Example 4. Clones with the largest insert size are selected for DNA sequence analysis. Clones found with a characteristic 5'-terminal sequence and an open reading frame that codes for a protein of approximately 120,000 M.W. are full-length bioadhesive precursor protein cDNA clones.

23

EXAMPLE 7

Construction of Expression Vector pGX2383 for Microbial Production of *M. edulis* Bioadhesive Precursor Protein The steps outlined below and illustrated schematically in FIG. 6 yielded a plasmid that expresses *M. edulis* bioadhesive precursor protein as a hybrid fusion protein. The presence of a methionine residue immediately on the amino-terminal side of the adhesive protein allows isolation of basically pure bioadhesive precursor protein sequence after cyanogen bromide cleavage (Gross, E., *Methods Enzymol.*, 11:238 (1967)). Plasmid pGX2287 (NRRL-B15788), part of a highly optimized vector/host system for expression of bovine chymosin (see copending U.S. Patent Application No. 644,998 and U.S. Pat. No. 4,798,791) was used as the starting vector.

The EcoRI fragment from lambda gt10 clone 14-1 was subcloned into the EcoRI site of plasmid pGX2627. Plasmid pGX2627 is derived from pGX1066 (on deposit at the American Type Culture Collection, Rockville, Maryland, and having accession number ATCC 39955). To derive pGX2627, a 514-base pair RsaI fragment from wild-type phage M13 containing the M13 origin of replication was inserted into the EcoRV site of pGX1066. The DNA sequence of pGX2627 is shown in FIG. 7.) This plasmid contains a multi-restriction site sequence as shown in FIG. 5(*a*). Ten micrograms of plasmid pGX2627 DNA and 20 micrograms of lambda clone 14-1 DNA were cut with EcoRI (New England Biolabs). This enzyme reaction and all those outlined below were performed according to the manufacturer's recommendations. The pGX2627 DNA was then treated with alkaline phosphatase. After phenol-chloroform extraction and ethanol precipitation using standard procedures in the art, a ligation using T4 DNA ligase in 20 ul with 1 ug of the EcoRI-cut, phosphatase-treated pGX2627 DNA and 12.5 ug EcoRI-treated lambda 14-1 DNA was started at 15° C. After 30 minutes, the reaction mixture was diluted to 50 ul and ligation was continued for nine hours. The ligation mix was used to transform *E. coli* DH1 (D. Hanahan, *J. Mol. Biol.* 166:557–580, 1983) using standard procedures (Mandol, M. and Higa, A., *J. Mol. Biol.*, 53:154, 1970). Most of the transformants contained the desired insert. One recombinant plasmid was identified as pGX2368 as shown in FIG. 6.

Plasmid pGX2346 was constructed from pGX2287 by insertion of a synthetic oligonucleotide (FIG. 5*b*) between the ClaI and SphI sites or pGX2287. Plasmid pGX2287 DNA was cut with ClaI and ligated with synthetic DNA at high molar concentration. The ligated DNAs were then cut with SphI and ligated again at low concentration to form circles. Plasmid pGX2346 was identified by its decreased size and verified by DNA sequencing.

An in-frame gene fusion between the trpB portion of pGX2346, and the bioadhesive precursor protein cDNA of pGX2368 is constructed in the following manner: A BclI endonuclease recognition site was first placed at the translation stop codon of pGX2368 by changing two bases as indicated in FIG. 1 using oligonucleotidedirected mutagenesis (Zoller, M.J. and M. Smith, *Methods Enzymol.*, 100:457–500, 1983) to create plasmid pGX2380. Both plasmids pGX2380 and pGX2346 are grown for DNA preparation in an *E. coli* host that contains the dam mutation (defective in DNA adenine methylase) so that they could digested with BclI. The non-methylated pGX2346 DNA is cut with NotI and the pGX2380 DNA is cut with XbaI. Then both DNAs are treated with *E. coli* DNA polymerase (Klenow fragment) to fill in the 5' single-stranded DNA overhangs. The DNAs are then ligated at high DNA concentration (approximately 2 ug of each DNA in 20 ul) with T4 ligase. The ligation product is cut with BclI then ligated again at low DNA concentration (approximately 1 ug total DNA in 150 ul volume) and used to transform *E. coli* GX3015. A transformant with the desired construction (see FIG. 6) is designated pGX2383. GX3015 cells with plasmid pGX2383 produce a bioadhesive precursor protein of approximately 24,000 M.W. upon induction of the hybrid lambda promoter by a shift of growth temperature from 32° to 37° C.

EXAMPLE 8

Construction of Expression Vector pGX2381, for Microbial Production of *M. edulis* Bioadhesive Precursor Protein The EcoRI insert fragment from lambda gt11 clone 52 (see FIG. 2) was cloned into the EcoRI site of plasmid pGX2627. Plasmid pGX2627 is derived from pGX1066 that has been deposited at the American Type Culture Collection (ATCC 39955). To derive plasmid pGX2627, a 514-base pair RsaI fragment from wild-type phage M13 containing the M13 origin of replication was inserted into the EcoRV site of pGX1066. The DNA sequence of pGX2627 is shown in FIG. 7.

Ten micrograms of plasmid pGX2627 DNA and twenty micrograms of lambda clone 52 DNA were cut with EcoRI. The pGX2627 DNA was then treated with alkaline phosphatase. After phenol-chloroform extraction and ethanol precipitation using standard procedures in the art, one microgram of phosphatase-treated pGX2627 DNA and twelve micrograms of the EcoRI-cut lambda clone 52 DNA were ligated at 15° C. in a twenty microliter volume with T4 polynucleotide ligase. After thirty minutes the ligation mixture was diluted to fifty microliters with ligation buffer and the reaction was continued for nine hours. The ligation mix was used to transform *E. coli* DH1 (D. Hanahan, *J. Mol. Biol.* 166:557–580, (1983)) using standard procedures (M. Mandel and A. Higa, *J. Mol. Biol.* 53:154, (1970)). Most of the transformants contained the desired insert. One recombinant plasmid with the cDNA inserted in the orientation depicted in FIG. 6 was identified as pGX2377.

A BclI endonuclease site was placed at the translation stop codon of the cDNA in pGX2377 by changing the two bases as indicated in FIG. 2 using oligonucleotide-directed mutagenesis (J.M. Zoller and M. Smith, *Methods Enzymol.* 100:457–500, (1983)) to create pGX2381. The mutagenic oligonucleotide had the DNA sequence ACAGATATTGATCACAATATTA.

EXAMPLE 9

Yeast Expression of Bioadhesive Precursor Protein (Clone 14-1)

YpGX265GAL4 is on deposit at the American Type Culture Collection, Rockville, Maryland, having accession number ATCC 67233.

The YpGX265GAL4 vector contains the following functional units:

Promoter—Hybrid derived from the *S. cerevisiae* GAL1 and MF-alpha 1 (alpha-factor) promoters. Permits galactose-regulated expression.

Regulatory gene—GAL4- encodes GAL4 protein, a positive regulator of the GAL1-MF-alpha 1 hybrid promoter. Derived from *S. cerevisiae*.

Terminator—derived from synthetic DNA-based on *S. cerevisiae* GAPDH transcription terminator.

Signal encoding sequence—Derived from synthetic DNA- based on *S. cerevisiae* PH05 signal. Codons designed substantially for usage preference in *S. cerevisiae*.

LEU2-d gene—Marker for plasmid selection in *S. cerevisiae*. Derived from plasmid pJDB207.

2-micron DNA—Derived from plasmid pJDB207. Provides plasmid replication origin for *S. cerevisiae*.

*E. coli* replication origin—Derived from pJDB207.

*E coli* selectable marker—Ampicillin resistance —derived from pJDB207.

Foreign genes are inserted between PH05 signal encoding sequence and the GAPDH terminator.

1. YpGX265GAL4 is digested with restriction endonuclease HindIII and the large and small DNA fragments are gel-purified. The small (3.65 Kb) fragment is saved for a later step. 2. The large HindIII fragment is digested with restriction endonuclease SmaI, generating two DNA fragments.

3. M13mp9 (commercially available) is digested with SmaI and HindIII and then treated with calf alkaline phosphatase.

4. The DNA molecules generated in steps 2 and 3 are ligated and used for transformation of *E. coli*. The transformants containing phage double-stranded DNA with the yeast promoter-terminator cassette are identified.

5. The recombinant phage double-stranded DNA is digested with restriction endonucleases EcoRV and BamHI and the large fragment (approximately 8kb) is gel-purified.

6. Plasmid pGX2380 (prepared in accordance with Example 7 and containing bioadhesive precursor protein cDNA) is digested with restriction endonuclease XbaI, and the single-stranded overhang is filled with the Klenow fragment of DNA polymerase.

7. The DNA fragment generated in step 5 is digested with BclI. The small DNA fragment (approximately 625bp) is gel-purified.

8. Two oligonucleotides of sequence:

```
5' ATCAAATCGATGGCGGCC and 5'
   GGCCGCCATCGATTTGAT
``` are annealed and used in a three-way ligation with the DNA fragments generated in steps 5 and 7.

9. *E. coli* transformants containing the desired phage DNA molecules are identified by restriction endonuclease digestion.

10. The phage DNA generated in step 9 is digested with restriction endonucleases SmaI and HindIII and the small fragment (approximately 1300bp) is gel-purified.

11. YpGX265GAL4 is digested with SmaI and HindIII and the large fragment is gel-purified 12. The DNA molecules generated in steps 10 and 11 are ligated and *E. coli* is transformed The desired plasmid, YpGX285, is identified by restriction endonuclease digestion.

13. YpGX285 is linearized with restriction endonuclease HindIII and treated with calf alkaline phosphatase.

14. The 3.65 kb GAL4-containing fragment from step 1 is ligated with the linearized YpGX285 generated in step 13.

15. *E. coli* is transformed and the desired plasmid, YpGX285GAL4, is identified by restriction endonuclease analysis.

16. Saccharomyces strains carrying mutations in the LEU2 structural gene are transformed with YpGX28-5GAL4 by standard methods. A suitable strain is AH22 (ATCC #38626).

17. The yeast strain is grown in YNBD medium to maintain the plasmid. The YNBD medium contains 0.7% yeast nitrogen base, 2% glucose, and 20 mg/liter L-histidine.

18. For production of the bioadhesive precursor protein the strain is grown in medium containing 1% yeast extract, 2% peptone, 1% glucose, and 1% galactose at 30° C. with shaking.

19. Production of the bioadhesive precursor protein is analyzed by Western Blot and SDS-polyacrylamide gel electrophoresis of the yeast proteins following procedures known in the art.

EXAMPLE 10

Growth of GX3015 (pGX2383) and Induction of Bioadhesive Precursor Protein Synthesis Cultures are maintained using growth temperatures of 30° C. with ampicillin at 100 ug/ml and/or medium lacking tryptophan to maintain nutritional selection. Plasmid pGX2383 contains the bla gene which encodes beta-lactamase providing ampicillin resistance, as well as the trpED that in tryptophan-deficient medium complements the trpED102 deletion in the GX3015 chromosome.

A single colony of GX3015 (pGX2383) is picked after growth on minimal salts medium (Miller, J.H., "Experiments in Molecular Genetics," Cold Spring Harbor Laboratory, 1972, p. 432) supplemented with 0.4% casamino acids and 0.4% glucose and inoculated into 5 ml of LB medium supplemented with 100 ug/ml ampicillin. After reaching an optical density ($A_{600}$) of greater than 1.0, 0.4 ml of the culture is inoculated into each of two 250-ml baffled flasks containing 50 ml of LB broth supplemented with 100 ug/ml ampicillin. The two flasks are incubated at 30° C. and shaken at 250 r.p.m. for 6.5 to 9 hours.

Fermentation is carried out using 8 liters of the following initial medium:

$(NH_4)_2SO_4$—30 g
$KH_2PO_4$—15 g
$K_2HPO_4$—5 g
Biotin (0.5 mg/ml in 95% ethanol)—12 xl tap water to 8 liters, autoclave The following additions are made after autoclaving to provide the initial medium:

$CaCl_2.2H_2O$—10 ml of 10% (w/v) sterile solution
glucose—360 ml of 50% (w/v) sterile solution
niacin—18 ml of 0.5% (w/v) sterile solution
Trace solution 1—90 ml
Trace solution 2—18 ml
Trace solution 3—1.8 ml The following fermentation conditions are maintained:
pH 7.0 (controlled by 5N $NH_4OH$, and 1N $H_3PO_4$)
Sparge rate—1vvm
Temperature—32° C.
Agitation rate—800 r.p.m.

In order to increase cell density prior to induction of expression, a system of broth supplementation with nutrients is undertaken. The feed solution is prepared as follows:

1000 g glucose with deionized water for final volume of 1700 mls is autoclaved. After autoclaving, there is added:
Trace solution 1—500 ml
Trace solution 2—100 ml
Trace solution 3—10 ml
$CaCl_2.2H_2O$—50 ml Trace Solution #1

$H_2O$—900 ml
conc HCl—13.1 ml
$FeCl_3.6H_2$—5.4 g
$ZnSO_4.7H_2O$—1.44 g
$MnCl_2.4H_2O$—1.0 g
$CuSO_4.5H_2O$—0.25 g
$CoCl_2.6H_2O$—0.24 g
$H_3BO_3$—0.062 g
Brought to 1000 ml and sterile filtered.

Trace Solution #2

$H_2O$—900 ml
Hcl—44.8 ml
$MgSO_4.7H_2O$—61.6 g
Brought to 1000 ml and sterile filtered.

Trace Solution #3

$H_2O$—1000 ml
$Na_2MoO_4.2H_2O$—24.1 g
Sterile filtered.

The feed solution is initially added to the broth in a volume of 180 ml and thereafter as needed to maintain the glucose level at 10 g/liter. Feed supplementation is continued until the $A_{600}$ reaches 20, at which time the cells are induced to express bioadhesive precursor protein from the hybrid lambda promoter. Induction is effected by raising the temperature to 37° C. to deactivate the temperature-sensitive lambda cI857 repressor protein produced by the defective lysogen in the GX3015 chromosome. The fermentation is maintained at 37° C. for another 6-8 hours.

EXAMPLE 11

Purification of Bioadhesive Precursor Protein

E. coli GX3015 (pGX2383) cells (32 g wet weight) are suspended in 20 ml 20 mM Tris-HCl, 2mM EDTA (pH 7.5), 1 mM phenylmethylsufonyl fluoride, 25 mM iodoacetic acid, and thoroughly disrupted by passage through a French press followed by sonication. The cell debris and protein-containing inclusion bodies containing bioadhesive precursor protein are pelleted by centrifugation at 27,500 g for 30 minutes at 4° C. The pellet is extensively washed by suspension in 10 mM Tris-HCl, 1 mM EDTA (pH 7.5) and centrifugation Washing is continued until the supernatant is clear The pellet is then dissolved in 15 ml of 6 M guanidine hydrochloride, 5% beta-mercaptoethanol, 25 mM iodoacetic acid, and centrifuged at 30,000 xg for 30 minutes at 4° C. The supernatant is dialyzed against 4 liters of 0.2 mM EDTA, 10 mM iodoacetic acid, with 3 changes which results in protein precipitation. The precipitate containing about 0.5 g of protein is dissolved in 40 ml of 70% formic acid. Cyanogen bromide (1.3 g) is added and the solution is allowed to react overnight at room temperature. After rotary evaporation, the residue is extracted with 20 ml water (pH 4.0 from residual formic acid). The pH of the water-soluble fraction is adjusted to pH 7.0 with 5N KOH resulting in some precipitate formation. The supernatant is then applied to a CM cellulose or S-Sepharose column (2.5×26 cm) equilibrated with 50 mM potassium phosphate (pH 7.5). After the column is washed for 14 hours with 50 mM potassium phosphate, the bioadhesive precursor protein is eluted with either a salt gradient (0 to 0.5 M KCl) or a pH change (pH 8 to pH 10) in the buffer. The fractions are assayed by measurement of absorbance at 280 nm and by SDS polyacrylamide gel electrophoresis using both coomassie blue protein stain and the Western blot assay with specific antibodies (Example 1). The fractions containing the bioadhesive precursor protein are pooled and dialyzed overnight twice against 2 liters of deionized water. The resultant suspension is lyophilized and 1 mg of purified material is obtained. Material could be further purified, if necessary, using Sephadex G-75 column chromatography with 0.3M ammonium acetate pH 4.0. Polyphenolic protein eluting in the first protein peak is dialyzed against water and lyophilized for recovering as a salt-free powder.

The purified protein is hydrolyzed in 6 M constant boiling HCl with phenol crystal in vacuo at 105° C. for 24 hours. The amino acids in the acid hydrolysate are identified as O-phthaldehyde (OPA) derivatives which are separated on $C_{18}$ reverse-phase HPLC column (Fleury, M.O. and D.V. Ashley, Anal. Biochem., 133:330-335 (1983)). The amino acid composition is used to verify purity since only a subset of amino acids is present in bioadhesive precursor protein.

EXAMPLE 12

Alternate Method for Bioadhesive Precursor Protein Purification

E. coli cells [GX3015 (pGX2383)]or yeast cells [AH2-2(YpGX285GAL4)]from a 180 l fermentation are centrifuged in a Westphalia centrifuge, washed with saline and resuspended as a 30% solids suspension in 10 mM EDTA, 1.0 mM phenylmethylsulfonyl fluoride (PMSF), 10 mM iodoacetic acid (IAA) at pH 8.0 before breaking by a Manton-Gaulin homogenizer. Bioadhesive precursor protein present in an insoluble fraction is collected with the cell debris upon Westphalia centrifugation. The centrifugation pellet is made a 20% solids suspension in acetic or formic acid at pH 2.2 to 2.5 and mixed for several hours to solubilize bioadhesive precursor protein. The extract is centrifuged or filtered to remove solids and the clear filtrate solution is then adjusted to pH 4 with 5 N KOH in the presence of 10 mM EDTA, 10 mM IAA and 1.0 mM PMSF. Impurities are removed as a precipitate by filtration or centrifugation. The polyphenolic protein in the clear supernatant is then concentrated by ultrafiltration (10,000 M.W. cutoff membrane) and subsequently lyophilized. After the residue (approximately 50-100 g) is dissolved in 1.2 liter of 70% formic acid, cyanogen bromide (100 g) is added and the solution is stirred for 24 hours at room temperature. The reaction mixture is then dried by rotary evaporation and the residue is dissolved in 50-100 ml 6 M guanidine hydrochloride at pH 8.0 and centrifuged at 30,000 g for 20 minutes at 4° C. The supernatant is chromatographed on a Sephacryl S-300 column equilibrated with the same solution. The fractions containing bioadhesive precursor protein are collected, adjusted to pH 4.0 with acetic acid, and dialyzed against water and recovered as a salt-free powder.

EXAMPLE 13

Hydroxylation of Bioadhesive Precursor Protein

Since tyrosinase has been known to catalyze the hydroxylation of tyrosine and oxidation of DOPA (Ito et al., *Biochem.*, 222:407–411 (1984); Marumo and Waite, *Biochem. Biophys. Acta*, 892:98–103 (1986)), mushroom tyrosinase or *Streptomyces antibioticus* tyrosinase can be used to enzymatically modify the homogenous *E. coli* or yeast-produced bioadhesive precursor protein. To a 1 ml mixture containing a 2 mg protein, 25 umole ascorbic acid and 0.05 M sodium phosphate between pH 5 to 7.5, 0.1 mg mushroom tyrosinase (Sigma Chemical Co.) is added. The mixture is allowed to react at room temperature for 3 hours. The kinetics of the hydroxylation process can be monitored by the colorimetric assay for DOPA and DOPA-derived quinone (Waite, J.H. and M.L. Tanzer, *Anal. Biochem.*, 111:131–136 (1981)). The product is further analyzed by amino acid analysis after acid hydrolysis as above (Example 9). After correcting for loss during the recovery process, amino acid analysis indicates approximately 40% of the tyrosine residues are converted to DOPA.

After hydroxylation, the pH of the solution is adjusted to 4 with acetic acid and the solution is dialyzed against 100 volumes of 5% acetic acid. The samples are rotatory-evaporated to reduce the volume. The tyrosinase is removed either by using a LH-Sephadex 60 column, which is eluted with 0.2 M acetic acid, or using a membrane filtration method (Amicon PM30, cut off of 30,000 M.W.).

An alternative purification scheme after hydroxylation is described below. After CNBr cleavage, the supernatant obtained at pH 7.0 (see Example 11) is acidified to between pH 5 and 7 in the presence of ascorbic acid or tropolone (Kahn, V. and A. Andrawis, *Phytochemistry*, 24:905–908 (1985)). Hydroxylation is started by the addition of tyrosinase. At the end of the reaction, the sample is purified by an SE Sephadex column. The fractions containing DOPA are pooled, dialyzed against 2.5% acetic acid and lyophilized. The purity of the hydroxylated protein is established by acid-urea polyacrylamide gel electrophoresis (Panyium S. and R. Chalkley, Arch. Biochem. Biophys., 30:337–346 (1969)) and amino acid analysis.

The DOPA-containing bioadhesive protein is then ready for formulation as an adhesive.

EXAMPLE 14

Used of Bioadhesive Protein as a Primer for Conventional Adhesives

Surfaces such as metals or plastics are frequently given a pretreatment such as oxidation with acid, flame treatment or plasma bombardment to improve the ability of a surface to "wet" or interact with the adhesive.

Microbially produced and hydroxylated mussel bioadhesive protein coated onto a surface can be used as a pretreatment or priming substance for conventional adhesives. An example of the use of mussel bioadhesive protein as a primer treatment for bonding two pieces of aluminum is given below.

Hydroxylated bioadhesive protein prepared as in Example 13 is dissolved in degassed water (optimally at pH 7.0 to 8.0) at a concentration of 10–400 mg/ml (10–40% w/v). The solution is maintained under nitrogen to prevent premature oxidation of DOPA residues to quinones and curing of the adhesive primer.

The bioadhesive protein solution is sprayed or painted to uniformly moisten an oil-free aluminum surface in a normal air environment. The surface is then dried in a low-humidity environment. A brown or tan color may develop indicating quinone oxidation and chemical cross-linking. The primed surfaces to be bonded are then joined using standard materials such as epoxy glue.

As an alternative to speed bioadhesive protein curing and eliminate the prehydroxylation step (see Example 13), an enzyme such as mushroom tyrosinase (Ito et al., *Biochemistry*, 222:407–411 (1984)) or Streptomyces tyrosinase (Lerch and Ettlinger, *Eur. J. Biochem.*, 31:427–437 (1972)) is mixed with the non-hydroxylated protein (Example 11) immediately prior to application (for example, in the nozzle of a spray applicator) at a concentration of 0.01 to 1.0 mg/ml solution. The enzyme under these conditions effects oxidation all the way from tyrosine to the reactive quinone species.

Blends of bioadhesive protein with other polymers (as outlined in adhesive examples given below) are also used as primers for other adhesives.

EXAMPLE 15

Use of Bioadhesive Protein

The hydroxylated bioadhesive protein prepared as in Example 13 is dissolved at a concentration of 1–700 mg/ml (0.1–70% solids) in water (or a physiological salt solution for medical applications) adjusted to pH 6.0 with dilute acids.

Immediately prior to application to a surface, a basic solution (approximately 1/50 volume) is added to increase the pH to 8.0. An enzyme such as mussel catechol oxidase (Waite, J.H., *J. Mar. Biol. Assoc.*, 65:359–371 (1985)) can also be added (final concentration 0.01–1 mg/ml) in place of or in addition to base solution immediately prior to application to accelerate the oxidation of DOPA residues to quinones to yield more rapid curing. Mixing of components immediately prior to application can occur, for example, in a spray head of a Duploject ® syringe as has been described for fibrin sealant (Redl, H. and G. Schlag, *Facial Plastic Surgery*, 2:315–321 (1985)). Alternative enzymes such as mushroom tyrosinase (Ito et al., *Biochemistry*, 222:407–411 (1984)) or Streptomyces tyrosinase (Learch and Ettlinger, Eur. J. Biochem., 31:427–437 (1972)) are also used. With tyrosinase, the bioadhesive protein need not be previously hydroxylated and thus the material without prior hydroxylation described in Example 11 may be used. In order for oxidation of DOPA residues to quinones to take place and subsequent curing (either with or without enzymes), there must be dissolved oxygen present in the bioadhesive protein solution.

EXAMPLE 16

Composites of Bioadhesive Protein with Other Protein Polymers

In order to moderate and improve the properties of the mussel polyphenolic protein adhesive, blends with other polymers are used. The bioadhesive protein is naturally associated with collagen in the byssal threads of the mussels. Collagen is one natural polymer that can be used to increase the cohesive strength of phenolic protein composites. Acid-soluble collagen (Gallop, P.M. and S. Seifter, *Methods Enzymol.*, VI:635-641 (1963)) is dissolved in dilute acid solution at 10-70% (w/v). The collagen is mixed with the bioadhesive protein mixtures as described in Example 15 in ratios having from 1% to 50% of the solids comprising bioadhesive protein with total solids ranging from 10 to 70%. Higher percentages of bioadhesive protein yield more highly cross-linked rigid composites than those with lower percentages of bioadhesive protein. Alkaline solution may be used to neutralize the mixture immediately prior to application. This allows more rapid oxidation and cross-linking (curing) of the mixture. Also, at neutral pH, the collagen will crystallize providing added cohesive strength.

Alternatively, the bioadhesive protein is used in combination with preformed sheets of collagen. This method is analogous to the use of reinforcing steel in cement or graphite fiber in epoxy composites. Collagen sheets such as the commercially available collastat (a Helitrex product distributed by American Home Products Corporation) or other similar products are sprayed or soaked in bioadhesive protein activated as described above in Example 13, then applied to the surface to be bonded.

In a similar manner, other types of insoluble or crystalline protein sheets can be used as reinforcement for adhesive protein. For example, silk cloth, or sheets formed from solubilized and reprecipitated alpha-keratose from wool keratin fibers (J. De Bersagbes, *Curr. Probl. Dermatol.*, 6:34-86 (1976)), or polymerized fibrin clot formed from purified fibrinogen, thrombin and Factor VIII (Redl, H. and G. Schlag, *Facial Plastic Surgery*, 2:315-321 (1985)) are used. For medical applications, the use of sheets of fibrin may have the additional benefit of helping to promote wound healing (Redl and Schlag, supra).

EXAMPLE 17

Composites of Bioadhesive Protein with Carbohydrate Polymers

Chitosan is dissolved in 1% acetic acid to a concentration of 30-150 mg/ml (3-15% w/v). The chitosan solution with a final pH of approximately 6.0 is blended with the bioadhesive protein solution described in Example 15. Blends typically have bioadhesive protein concentrations between 2 and 30% and chitosan concentrations between 1 and 7%. At pH 6.0 where the chitosan is still soluble, catechol oxidase and tyrosinase addition catalyzes the formation of reactive DOPA-derived quinones and cross-linking. Increasing the pH to 8.0 as in Example 15 prior to application results in the immediate precipitation of chitosan out of solution which in some cases may not be desirable.

EXAMPLE 18

Isolation of DNA Clone N1 Encoding M. edulis Bioadhesive Precursor Protein

Messenger RNA was isolated from fresh *M. edulis* as described in Example 6. Two 18-base probes were synthesized based on the DNA sequence in clone 14-1. The first synthetic probe (#2214 - GTTTGTTGGTTTATATGC) was complementary to a conserved sequence close to the 3'-end of the coding sequence. This oligonucleotide was also used to prime cDNA synthesis. The second probe (#2213 -TTTATAAGTTGGCTTTGC) was the complement of the sequence that codes for the hexapeptide found in several locations in the cDNA clones. Probes 2213 and 2214 were used together since they have the same GC/AT ratio and thus approximately the same melting temperature. The use of both probes provided multiple hybridization points and a strong signal during clone bank screening.

The clone bank prepared as in Example 6 was screened with the 18-base oligonucleotides. Thirty hybridization-positive clones were initially identified in duplicate. Twenty-eight of those were plaque purified with two rounds of plating and screening, and their DNA was analyzed. A third synthetic 18-base probe (#2231-GGGATATATTGACTTGGA), which encodes a portion of an uncommon, variant decapeptide, was included in this hybridization analysis.

As expected, many of the clones had larger cDNA inserts than in the cDNA cloning experiments described in Example 4: The largest clones, for example N5, N14 and N26, had a primary insert fragment of approximately 2.6 kb. Clones N1, N14 and N15 were chosen for initial DNA sequence analysis because these DNA preparations were the cleanest. Clone N1 had the largest insert that hybridized to all three probes and it displayed an intense signal with probe #2213, which encodes the predominant hexapeptide sequence.

An initial sequence analysis of two of the largest clones (N15 and N14) showed that both were false positives for polyphenolic protein sequence. The 2.1 kb EcoRI insert from clone N1 was sequenced as described in Example 6, with the following modifications. The N1 clone could be subcloned stably in only one orientation in the M13 sequencing vectors and the progressive sequencing strategy of Dale et al., *Plasmid*, Vol. 13, p. 31-40, (1985) was performed on only one strand. To confirm that the sequence was assembled correctly, the inserts from the series of overlapping subclones from the Dale procedure were sized by electrophoresis on agarose gels.

DNA sequencing confirmed that clone N1 contains polyphenolic protein cDNA. In fact, this clone appears to encode a very large middle portion of the mussel adhesive protein and contains 76 continuous tandem repeats of decapeptides and hexapeptides throughout the 2.1 kb length of the clone (FIG. 9). Gaps in the sequence shown in FIG. 9 allow optimal alignment of the hexapeptides with the decapeptides. Of the 63 decapeptides in the N1 protein, 31 are identical to the decapeptide described in U.S. Pat. No. 4,585,585. The variations in each position are shown in FIG. 10. Of the 13 hexapeptides, 10 are Ala-Lys-Pro-Thr-Tyr-Lys, two have Ser instead of Ala, and one has Val instead of Ala.

Clone N1 does not have a perfect overlap with any of the other cDNA clones sequenced to date. While it is possible that N1 lies just upstream of carboxy-terminal clones 52 or 14-1, it is also possible that the lack of perfect overlap in any of these clones is the result of multiple polyphenolic protein genes or alternate splicing patterns, as found in the studies of other structural proteins. Clone N1 also does not have a characteristic 5'-end sequence and therefore probably does not encode the N-terminus. However, it encodes a polyphenolic protein of nearly 80,000 molecular weight and therefore constitutes the majority of the 110,000-130,000 intact mussel protein.

Except for the proline-rich segment of clone 52, these sequencing results suggest that the tandem deca-and hexapeptide repeats may constitute the complete functional part of this protein with respect to adhesive properties. One could easily increase the size of the encoded protein by ligating two or more of the sequenced cDNA segments together.

EXAMPLE 19

Expression of Nl cDNA in Yeast

For expression of the Nl cDNA in yeast, it was desirable to position NotI and BamHI restriction endonuclease sites at the 5' and 3' ends of the coding sequence respectively. To accomplish this, vector M13mp18 was first mutagenized by oligonucleotide directed mutagenesis to insert a NotI site adjacent to the unique EcoRI site. An oligonucleotide of sequence.

5'   CCGAGCTCGAATTCTCGCGGCCGCGTAATCATGGTCAT was used to prime this mutagenesis.

The new M13 vector was called MGX463 and has unique NotI and BAMHI restriction sites bordering the EcoRI site. MGX463 double-stranded DNA was digested with EcoRI and treated with calf-alkaline phosphatase and the linear DNA was purified on a 0.8% agarose gel.

The Nl cDNA coding sequence was removed from an M13mp10 vector by digesting double-stranded DNA with EcoRI. The approximately 2200 base pair EcoRI fragment was gel purified. This fragment was ligated with the MGX463 double-stranded DNA which was linearized with EcoRI and treated with calf alkaline phosphatase. *E. coli* strain GX1210 was transformed with the ligacarries mix. This resulted in vector MGX464 which carries the Nl cDNA sequence bordered by NotI and BamHI restriction sites. MGX464 was digested with NotI and BamHI and the Nl cDNA fragment was gel purified.

Figure 11:
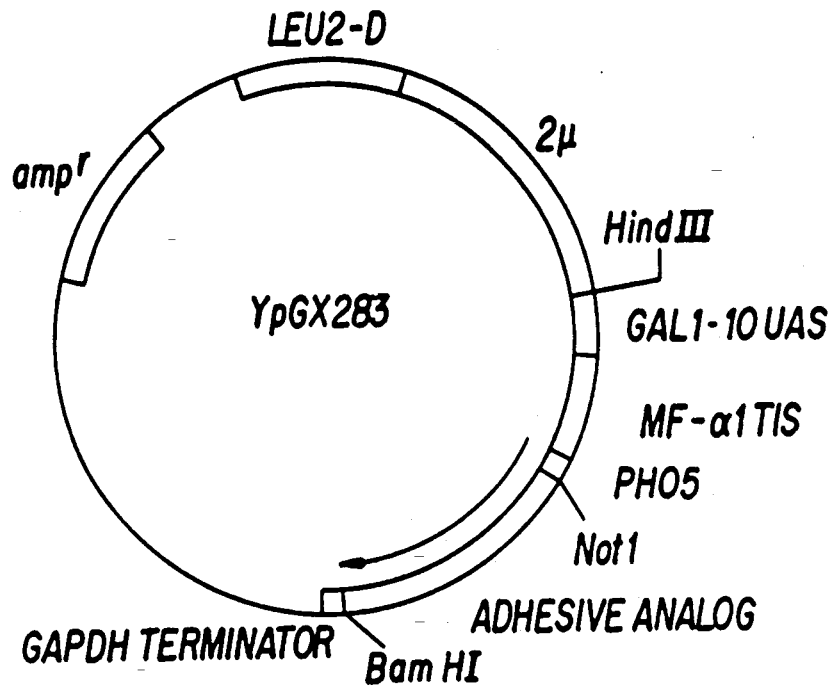
FIG. 11 is a restriction map of YpGX283, showing the position and orientation of the major functional elements.
Figure 12:
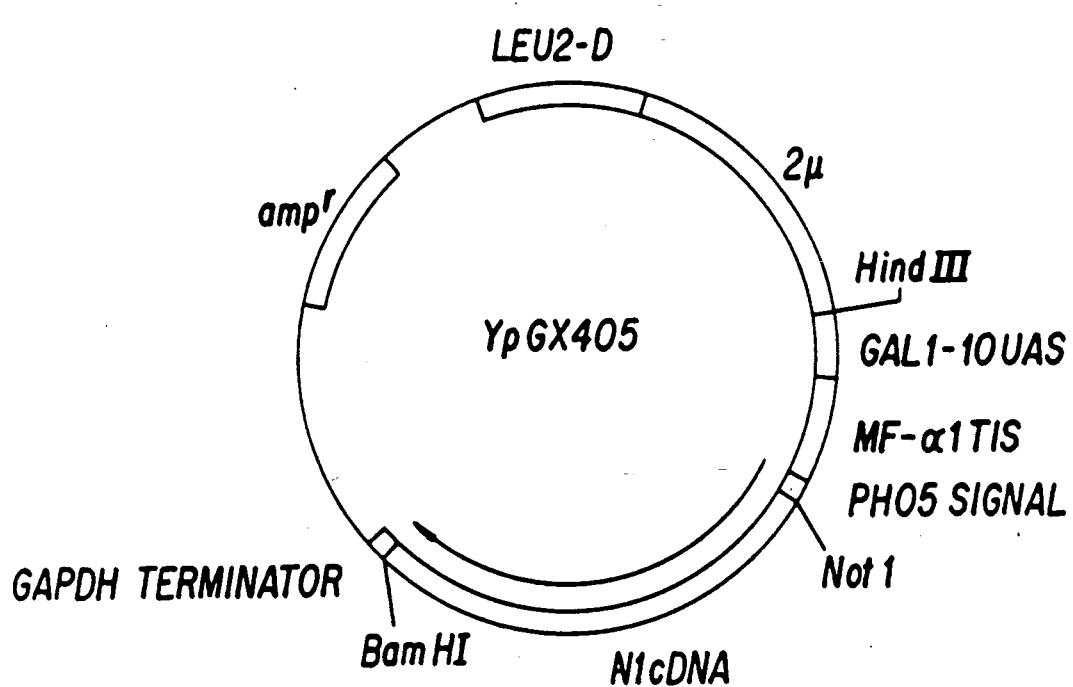
FIG. 12 is a restriction map of plasmid YpGX405 yeast *E. coli* shuttle vector, showing the position and orientation of major functional elements.

YpGX283 (fully described in commonly assigned co-pending U.S. Pat. Application Ser. No. 025,243, filed March 12, 1987, and shown in FIG. 11) was digested with NotI and BamHI and the large vector fragment was gel purified. This fragment was ligated with the NotI/BamHI Nl cDNA fragment and *E. coli* strain GX1210 was transformed, resulting in plasmid YpGX405. Plasmid YpGX405 (FIG. 12) is a yeast *E. coli* shuttle vector which contains the Nl cDNA sequence positioned between the PH05 signal coding sequence and the GAPDH transcription terminator. Expression is directed by a hybrid promoter composed of elements of the yeast GAL1 and MF-alpha 1 promoters. In order to insert the GAL4 gene into YpGX405, that plasmid was linearized with HindIII and treated with calf alkaline phosphatase. Vector YpGX283GAL4 (fully described in co-pending commonly assigned U.S. Pat. Application Ser. No. 025,243, filed March 12, 1987), was digested with HindIII and the GAL4 gene was gel purified. These two fragments were ligated and *E. coli* strain GX1210 was transformed, resulting in YpGX405GAL4.

To determine if *S. cerevisiae* produced bioadhesive precursor protein of the expected molecular weight, yeast strain D8 transformed with expression vector YpGX405GAL4 first grown on YNBD solid medium (0.7% yeast nitrogen base, 10% glucose, 2% agar) and then inoculated into 10 ml YPD (1% yeast extract, 2% peptone, 2% glucose) so that the initia $A_{600}$ reading was 0.1 and was then grown at 28° C. with shaking for 17-24 hours. The cells were harvested and washed with 10 ml YPGal (1% yeast extract, 2% peptone, 2% galactose) and resuspended in an equal volume of YPGal and induced for 6-28 hours. One ml of that culture was harvested and washed with $T_{25} E_{125}$ pH 8.4 buffer (25 mM Tris-HCl, 125 mM EDTA, pH 8.4). The cells were then resuspended in 100 ul $T_{25} E_{125}$ buffer, and broken by vortexing in the presence of glass beads. Following the addition of 200 ul $T_{25} E_{125}$, the cell lysate was removed from the glass beads and cell debris was pelleted in a microfuge for five minutes. The insoluble pellet was resuspended in 200 ul sample buffer (Laemmli, U.K. 1970, *Nature* 227:680–685) and boiled for five minutes. A 25 ul aliquot was examined on a 10% SDS-polyacrylamide gel and stained with Coomassie blue. The results of this analysis showed that bioadhesive precursor protein of the appropriate molecular weight was produced by the yeast strain at levels of approximately one percent of the total cell protein.

EXAMPLE 20

Purification of Bioadhesive Precursor Protein

Yeast cells as a 30% suspension in 20 mM Tris pH 7.5, 2 mM EDTA, 0.1 mM PMSF, 10 mM iodoacetic acid were thoroughly disrupted mechanically by a French Press, sonicator or a Manton Gaulin homogenizer. The adhesive precursor protein present in the insoluble fraction was collected with cell debris by centrifugation at 25,000 g for 30' at 4° C. The pellet was extensively washed with 10 mM Tris, 1 mM EDTA (pH 7.8) and centrifuged as before. The pellet was resuspended as a 30% suspension in formic acid (final concentration of 70%) and mixed for several hours. Cyanogen bromide (50 gm/l) was added and the suspension was stirred for 24 hours at room temperature. The reaction mixture was then rotary evaporated to dryness, and the residue was resuspended to the original lysis volume with water (pH 3.0) and stirred for several hours to extract the adhesive protein.

After centrifugation (as before), the adhesive precursor protein was precipitated from the supernatant with 10% NaCl. The precipitate was then dissolved in guanidinium chloride (final concentration 6 M, pH 8.0) with 5% 2-mercaptoethanol and chromatographed on a Sephacryl S-300 or S-400 column, depending on the size of the adhesive precursor protein. The fractions containing the adhesive precursor protein were pooled, adjusted to pH 4.0 with glacial acetic acid, dialyzed against 5% acetic acid, then 0.1% acetic acid, with several changes of the dialysis solution, and lyophilized.

The purified protein was characterized by its mobility on SDS-polyacrylamide gel electrophoresis using both Coomassie blue stain and Western blot analysis, its UV absorption spectrum, protein quantitation and amino acid composition analysis.

EXAMPLE 21

The yeast cells were processed as in Example 20 up to the 10% NaCl precipitation step. Instead of treating with NaCl, the supernatant was adjusted to pH 5.2 and centrifuged. The clear supernatant was dialyzed against 10% formic acid and slowly to water and then to 30 mM phosphate buffer (pH 7.3). After centrifugation, the supernatant was chromatographed on a weak cation exchanger. The column was eluted first with a 0.2-1 M salt gradient at pH 7.3, followed by 1M NaCl in 5% acetic acid. The fractions containing the adhesive precursor protein were pooled, dialyzed and lyophilized as in Example 20, and the identity and purity of the adhesive precursor protein were determined as described in Example 20.

EXAMPLE 22

After the yeast cells were broken and centrifuged as in Example 20, the pellet was solubilized in either 6 M guanidinium chloride or 8 M urea with 5% 2-mercaptoethenol. The insoluble cellular components were removed by centrifuging at 25,000 g for 30' at 4° C. The protein in the supernatant was precipitated by dialysis against water, and the adhesive precursor protein was extracted by a dilute formic acid or acetic acid solution (pH 2.0) for several hours. The adhesive precursor protein was precipitated by either adjusting the pH to neutral, or making the solution 10% NaCl. After centrifugation, the adhesive precursor protein pellet was dissolved in 6M guanidinium chloride and chromatographed on an S-300 or S-400 column depending on the size of the protein. The adhesive precursor protein, with the correct size, was pooled, adjusted to pH 4.0 with acetic acid, dialyzed against 5% acetic acid then 0.1% acetic acid and lyophilized.

EXAMPLE 23

The yeast cells were broken and thoroughly washed as in Example 20. The pellet was extracted for several hours with dilute formic or acetic acid (pH 2.0). The solution was then adjusted to pH 3.0 and centrifuged. The adhesive precursor protein present in the supernatant was precipitated when the pH was adjusted to between 5.0 and 5.5. The adhesive precursor protein was collected by centrifugation, and, if necessary, further purified by either a weak cation exchange, or a gel filtration column as described in Examples 20 and 21.

What is claimed is:

1. An isolated DNA segment comprising codons which encode the native amino acid sequence of a bioadhesive precursor protein of a marine animal selected from the group consisting of mussels and barnacles, said protein being capable of function as a bioadhesive after expression and upon hydroxylation and oxidation, or an isolated DNA segment comprising codons which encode the native amino acid sequence of a fragment of said protein, said fragment being capable of function as a bioadhesive after expression and upon hydroxylation and oxidation 2. A DNA segment as claimed in claim 1 wherein said marine animal is a mussel.

3. A DNA segment as claimed in claim 2 wherein said mussel is of the genus Mytilus.

4. A DNA segment as claimed in claim 3, wherein the encoded bioadhesive precursor protein is of the mussel species *Mytilus edulis.*

5. A DNA segment as claimed in claim 4 comprising codons for a bioadhesive precursor protein which contains the sequence:

Lys Leu Ser Ser Tyr Lys Pro Ile Lys Thr Thr Tyr Asn Ala Lys Thr Asn Tyr Pro Pro Val Tyr Lys Pro Lys Met Thr Tyr Pro Pro Thr

Tyr Lys Pro Lys Pro Ser Tyr Pro Pro Thr Tyr Lys Ser Lys Pro Thr Tyr Lys Pro Lys Ile Thr Tyr Pro Pro Thr Tyr Lys Ala Lys Pro

Ser Tyr Pro Pro Thr Tyr Lys Pro Lys Lys Thr Tyr Pro Pro Thr Tyr Lys Pro Lys Leu Thr Tyr Pro Pro Thr Tyr Lys Pro Lys Pro Ser

Tyr Pro Pro Thr Tyr Lys Ser Lys Pro Thr Tyr Lys Pro Lys Ile Thr Tyr Pro Pro Thr Tyr Lys Ala Lys Pro Ser Tyr Pro Pro Thr Tyr

Lys Pro Lys Lys Thr Tyr Pro Pro Thr Tyr Lys Pro Lys Leu Thr Tyr Pro Pro Thr Tyr Lys Pro Lys Ala Ser Tyr Pro Pro Thr Tyr Lys

Pro Lys Pro Ser Tyr Pro Pro Ser Tyr Lys Thr Lys Lys Thr Tyr Pro Pro Thr Tyr Lys Pro Lys Leu Thr Tyr Pro Pro Thr Tyr Lys Pro

Lys Pro Ser Tyr Pro Pro Ser Tyr Lys Pro Lys Lys Thr Tyr Pro Pro Thr Tyr Lys Pro Lys Leu Thr Tyr Pro Pro Thr Tyr Lys Ala Lys

Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro

Ser Tyr Pro Ser Thr Tyr Lys Ala Lys Pro Ser Tyr Pro Pro Thr Tyr Lys Ala Lys Pro Thr Tyr Lys Ala Lys Pro Thr Tyr Lys Ala Lys

Pro Thr Tyr Pro Ser Thr Tyr Lys Ala Lys Pro Thr Tyr Pro Pro Thr Tyr Lys Ala Lys Pro Ser Tyr Pro Pro Thr Tyr Lys Ala Lys Pro

Thr Tyr Lys Ala Lys Pro Thr Tyr Lys Ala Lys Pro Ser Tyr Pro Pro The Tyr Lys Ala Lys Pro Ser Tyr Pro Pro Thr Tyr Lys Ala Lys

Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Val Lys Pro

Thr Tyr Lys Ala Lys Pro Thr Tyr Pro Ser Thr Tyr Lys Ala Lys Pro Ser Tyr Pro Pro Thr Tyr Lys Ala Lys Pro Ser Tyr Pro Pro Thr

Tyr Lys Ala Lys Pro Ser Tyr Pro Pro Thr Tyr Lys Ala Lys Pro Ser Tyr Pro Pro Thr Tyr Lys Ala Lys Pro Thr Tyr Pro Ser Thr Tyr

Lys Ala Lys Pro Ser Tyr Pro Pro Thr Tyr Lys Pro Lys Ile Ser Tyr Pro Pro Thr Tyr Lys Ala Lys Pro Ser Tyr Pro Ser Thr Tyr Lys

Ala Lys Ser Ser Tyr Pro Pro Thr Tyr Lys Ala Lys Pro Ser Tyr Pro Pro Thr Tyr Lys Ala Lys Pro Thr Tyr Pro Ser Thr Tyr Lys Ala

Lys Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro

Pro Thr Tyr Lys Ala Lys Pro Thr Tyr Lys Ala Lys Pro Thr Tyr Lys Ala Lys Pro Thr Tyr Pro Ser Thr Tyr Lys Ala Lys Pro Ser Tyr

Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro

Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro

Thr Tyr Lys Ala Lys Pro Thr Tyr Lys Ala Lys Pro Thr Tyr Pro Ser Thr Tyr Lys Ala Lys Pro Ser Tyr Pro Pro Thr Tyr Lys Ala Lys

Pro Ser Tyr Pro Pro Thr Tyr Lys Ala Lys Pro Ser Tyr Pro Pro Thr Tyr Lys Ala Lys Pro Thr Tyr Lys Ala Lys Pro Thr Tyr Pro Ser

Thr Tyr Lys Ala Lys Pro Ser Tyr Pro Pro Thr His Lys Ala Lys Pro Thr Tyr Lys Ala Lys Pro Thr Tyr Pro Ser Thr Tyr Lys Ala Lys

Pro Thr Tyr Pro Ser Thr Asp Gly Ala Lys Ser, or a fragment of said sequence, said fragment encoding a protein capable of function as a bioadhesive after expression and upon hydroxylation and oxidation.

6. A DNA segment as claimed in claim 4, coding for a bioadhesive precursor protein having the amino acid sequence:

Lys Pro Lys Pro Ser Tyr Pro Pro Ser Tyr Lys

Pro Lys Thr Thr Tyr Pro Pro Thr Tyr Lys Pro Lys Ile Ser

Tyr Pro Pro Thr Tyr Lys Ala Lys Pro Ser Tyr Pro Ala Thr

Tyr Lys Ala Lys Pro Ser Tyr Pro Pro Thr Tyr Lys Ala Lys

Pro Ser Tyr Pro Pro Thr Tyr Lys Ala Lys Pro Ser Tyr Pro

Pro Thr Tyr Lys Ala Lys Pro Thr Tyr Lys Ala Lys Pro Thr

Tyr Pro Pro Thr Tyr Lys Ala Lys Pro Ser Tyr Pro Pro Thr

Tyr Lys Pro Lys Pro Ser Tyr Pro Pro Thr Tyr Lys Ser Lys

Ser Ile Tyr Pro Ser Ser Tyr Lys Pro Lys Lys Thr Tyr Pro

Pro Thr Tyr Lys Pro Lys Leu Thr Tyr Pro Pro Thr Tyr Lys

Pro Lys Pro Ser Tyr Pro Pro Ser Tyr Lys Pro Lys Ile Thr

Tyr Pro Ser Thr Tyr Lys Leu Lys Pro Ser Tyr Pro Pro Thr

Tyr Lys Ser Lys Thr Ser Tyr Pro Pro Thr Tyr Asn Lys Lys

Ile Ser Tyr Pro Ser Ser Tyr Lys Ala Lys Thr Ser Tyr Pro

Pro Ala Tyr Lys Pro Thr Asn Arg Tyr or a fragment of said sequence, said fragment encoding a protein capable of function as a bioadhesive after expression and upon hydroxylation and oxidation.

7. A DNA segment as claimed in claim 4, coding for a bioadhesive precursor protein having the amino acid sequence:

Leu Pro Pro Ala Pro Pro Ala Pro Ala Phe Ala

Pro Ala Pro Ala Leu Ala Pro Ala Pro Pro Asn Pro Asn Pro

Pro Ser Pro Pro Ser Pro Pro Ser Pro Pro Thr Pro Pro Pro

Thr Pro Pro Ser Pro Pro Ala Pro Pro Ser Pro Pro Pro Ser

Pro Pro Asn Pro Pro Pro SEr Pro Pro Pro Ser Pro Pro Phe

Pro Pro Ala Pro Pro Pro Ser Pro Pro Phe Pro Pro Thr Tyr

Lys Ala Lys Pro Thr Tyr Lys Ala Lys Pro Thr Asn Pro Ser

Thr Tyr Lys Ala Lys Pro Ser Tyr Pro Pro Thr Tyr Lys Ala

Lys Pro Ser Tyr Pro Pro Thr Tyr Lys Ala Lys Pro Ser Tyr

Pro Pro Thr Tyr Lys Ala Lys Pro Thr Tyr Lys Ile Lys Pro

Thr Tyr Pro Ser Thr Tyr Lys Ala Lys Pro Thr Asn Pro Ser

Thr Tyr Lys Ala Lys Pro Ser Tyr Pro Pro Thr Tyr Lys Ala

Lys Pro Ser Tyr Pro Pro Thr Tyr Lys Ala Lys Pro Ser Tyr

Pro Pro Thr Tyr Lys Ala Lys Pro Thr Tyr Lys Ile Lys Pro

Thr Tyr Pro Ser Thr Tyr Lys Ala Lys Pro Thr Tyr Lys Ala

Lys Pro Thr Tyr Pro Pro Thr Tyr Lys Ala Lys Pro Ser Tyr

Pro Pro Thr Tyr Lys Pro Lys Pro Ser Tyr Pro Pro Thr Tyr

Lys Ser Lys Ser Ile Tyr Pro Ser Ser Tyr Lys Pro Lys Lys

Thr Tyr Pro Pro Thr Tyr Lys Pro Lys Leu Thr Tyr Pro Pro

Thr Tyr Lys Pro Lys Pro Ser Tyr Pro Pro Ser Tyr Lys Pro

Lys Ile Thr Tyr Pro Ser Thr Tyr Lys Leu Lys Pro Ser Tyr

Pro Pro Thr Tyr Lys Ser Lys Thr Ser Tyr Pro Pro Thr Tyr

Asn Lys Lys Ile Ser Tyr Pro Ser Ser Tyr Lys Ala Lys Thr

Ser Tyr Pro Pro Ala Tyr Lys Pro Thr Asn Arg Tyr or a fragment of said sequence, said fragment encoding a protein capable of function as a bioadhesive after expression and upon hydroxylation and oxidation.

8. A DNA segment as claimed in claim 4, coding for a bioadhesive precursor protein having the amino acid sequence:

Tyr Lys Ala Lys Pro Ser Tyr Pro Pro Thr Tyr Lys Ala

Lys Pro Thr Tyr Lys Ala Lys Pro Thr Asn Pro Ser Thr

Tyr Lys Ala Lys Pro Ser Tyr Pro Pro Thr Tyr Lys Ala

Lys Pro Ser Tyr Pro Pro Thr Tyr Lys Ala Lys Pro Ser

Tyr Pro Pro Thr Tyr Lys Ala Lys Pro Thr Tyr Lys Ala

Lys Pro Thr Tyr Pro Ser Thr Tyr Lys Ala Lys Pro Thr

Tyr Lys Ala Lys Pro Thr Tyr Pro Pro Thr Tyr Lys Ala

Lys Pro Ser Tyr Pro Pro Thr Tyr Lys Pro Lys Pro Ser

Tyr Pro Pro Thr Tyr Lys Ser Lys Ser Ile Tyr Pro Ser

Ser Tyr Lys Pro Lys Lys Thr Tyr Pro Pro Thr Tyr, or a fragment of said sequence, said fragment encoding a protein capable of function as a bioadhesive after expression and upon hydroxylation and oxidation.

9. A DNA segment as claimed in claim 4, coding for a bioadhesive precursor protein having the amino acid sequence:

Thr Ser Thr Tyr Lys Ala Lys Pro Ser Tyr Pro Pro Thr

Tyr Lys Ala Lys Pro Thr Tyr Pro Ser Thr Tyr Lys Ala

Lys Pro Ser Tyr Pro Pro Thr Tyr Lys Pro Lys Ile Ser

Tyr Pro Pro Thr Tyr Lys Ala Lys Pro Ser Tyr Pro Pro

Thr Tyr Lys Ala Lys Pro Ser Tyr Pro Pro Thr Tyr Lys

Ala Lys Pro Thr Tyr Lys Ala Lys Pro Thr Asn Pro Ser

Thr Tyr Lys Ala Lys Pro Ser Tyr, or a fragment of said sequence, said fragment encoding a protein capable of function as a bioadhesive after expression and upon hydroxylation and oxidation.

10. A DNA segment as claimed in claim 4, comprising the following DNA sequence:

AAG CTG TCA TCT TAC AAA CCT ATT AAG ACA ACA TAT AAT GCA AAG ACA AAT TAT CCA CCA
GTT TAT AAA CCT AAG ATG ACT TAT CCT CCT ACA TAC AAA CCA AAG CCC AGT TAT CCT CCA
ACA TAT AAA TCA AAG CCC ACA TAC AAA CCT AAG ATA ACA TAC CCT CCA ACT TAT AAA GCA
AAG CCC AGT TAT CCT CCA ACA TAT AAA CCT AAG AAA ACT TAT CCC CCC ACA TAT AAA CCT
AAA CTA ACC TAT CCT CCT ACA TAC AAA CCA AAG CCC AGT TAT CCT CCA ACA TAT AAA TCA
AAG CCC ACA TAC AAA CCT AAG ATA ACA TAC CCT CCA ACA TAT AAA GCA AAG CCA AGT TAT
CCT CCT ACA TAT AAA CCT AAG AAA ACT TAT CCC CCC ACA TAT AAA CCT AAA CTA ACC TAT
CCT CCT ACA TAT AAA CCA AAG GCC AGT TAT CCT CCA ACA TAT AAA CCA AAA CCA AGT TAT
CCC CCT TCA TAT AAA ACT AAG AAA ACT TAT CCC CCC ACA TAT AAA CCT AAA CTA ACC TAT
CCT CCT ACA TAT AAA CCA AAA CCA AGT TAT CCC CCT TCA TAC AAA CCT AAG AAA ACT TAT
CCC CCC ACA TAT AAA CCT AAA CTA ACC TAT CCT CCT ACA TAT AAA GCA AAG CCA AGT TAT
CCT CCA ACA TAT AAA GCA AAA CCA AGT TAT CCT CCA ACT TAT AAA GCA AAA CCA AGT TAT
CCT CCA ACA TAT AAA GCA AAA CCA AGT TAT CCT TCA ACT TAT AAA GCA AAA CCA AGT TAT
CCT CCA ACT TAT AAA GCA AAG CCA ACT TAT AAA GCA AAG CCA ACT TAT AAA GCA AAG CCA
ACT TAT CCT TCA ACG TAT AAA GCA AAG CCA ACT TAT CCT CCA ACT TAT AAA GCA AAA CCA
AGT TAT CCT CCA ACT TAT AAA GCA AAG CCA ACT TAT AAA GCA AAG CCA ACT TAT AAA GCA
AAG CCA AGT TAT CCT CCA ACT TAT AAA GCA AAA CCA AGT TAT CCT CCA ACT TAT AAA GCA
AAG CCA AGT TAT CCT CCA ACG TAT AAA GCA AAG CCA AGT TAT CCT CCA ACT TAT AAA GCA
AAA CCA AGT TAT CCT CCA ACT TAT AAA GTA AAG CCA ACA TAT AAA GCA AAA CCA ACT TAT
CCT TCA ACG TAT AAA GCA AAG CCA AGT TAT CCT CCA ACT TAT AAA GCA AAA CCA AGT TAT
CCT CCA ACT TAT AAA GCA AAA CCA AGT TAT CCT CCA ACG TAT AAA GCA AAA CCA AGT TAT
CCT CCA ACT TAT AAA GCA AAA CCA ACT TAT CCT TCA ACG TAT AAA GCA AAA CCA AGT TAT
CCT CCA ACT TAT AAA CCT AAA ATA AGT TAT CCT CCA ACT TAT AAA GCA AAA CCA AGT TAT
CCT TCA ACT TAT AAA GCA AAA TCA AGT TAT CCT CCA ACT TAT AAA GCA AAA CCA AGT TAT
CCT CCA ACT TAT AAA GCA AAG CCA ACT TAT CCT TCA ACG TAT AAA GCA AAG CCA ACT TAT
AAA GCA AAG CCA AGT TAT CCT CCA ACG TAT AAA GCA AAG CCA AGT TAT CCT CCA ACT TAT
AAA GCA AAA CCC AGT TAT CCT CCA ACT TAT AAA GCA AAG CCA ACT TAT AAA GCA AAG CCA
ACT TAT AAA GCA AAG CCA ACT TAT CCT TCA ACG TAT AAA GCA AAG CCA AGT TAT CCT CCA
ACT TAT AAA GCA AAA CCA AGT TAT CCT CCA ACT TAT AAA GCA AAA CCA AGT TAT CCT CCA
ACT TAT AAA GCA AAA CCA AGT TAT CCT CCA ACT TAT AAA GCA AAG CCA AGT TAT CCT CCA
ACG TAT AAA GCA AAG CCA AGT TAT CCT CCA ACT TAT AAA GCA AAA CCA AGT TAT CCT CCA
ACT TAT AAA GCA AAG CCA ACT TAT AAA GCA AAG CCA ACT TAT CCT TCA ACG TAT AAA GCA
AAG CCA AGT TAT CCT CCA ACT TAT AAA GCA AAA CCA AGT TAT CCT CCA ACT TAT AAA GCA
AAA CCA AGT TAT CCT CCA ACT TAT AAA GCA AAA CCA ACT TAT AAA GCA AAG CCA ACT TAT
CCT TCA ACG TAT AAA GCA AAA CCA AGT TAT CCT CCA ACT CAT AAA GCA AAA CCA ACT TAT
AAA GCA AAG CCA ACT TAT CCT TCA ACT TAT AAA GCA AAA CCA ACT TAT CCT TCA ACG GAT
GGA GCA AAA TCA.

or a fragment of said sequence, said fragment encoding a protein capable of function as a bioadhesive after expression and upon hydroxylation and oxidation.

11. A DNA segment as claimed in claim 4, comprising the following DNA sequence:

AAA CCA AAA CCA AGT TAT CCA CCA TCT TAT AAA CCT AAA ACA ACT TAT CCT

CCA ACT TAT AAA CCT AAG ATA AGT TAT CCT CCA ACT TAT AAA

GCA AAA CCA AGT TAT CCA GCA ACT TAT AAA GCA AAA CCA AGT

TAT CCT CCA ACT TAT AAA GCA AAA CCA AGT TAT CCT CCA ACT

TAT AAA GCA AAA CCA AGT TAT CCT CCA ACT TAT AAA GCA AAG

CCA ACT TAT AAA GCA AAG CCA ACT TAT CCT CCA ACT TAT AAA

GCA AAA CCA AGT TAT CCT CCA ACA TAT AAA CCA AAG CCA AGT

TAT CCT CCA ACT TAT AAA TCC AAG TCA ATA TAT CCC TCT TCA

TAC AAA CCT AAG AAA ACT TAT CCC CCC ACA TAT AAA CCT AAA

CTA ACC TAT CCT CCA ACA TAT AAA CCA AAG CCA AGT TAT CCA

CCA TCT TAT AAA CCT AAG ATT ACT TAT CCC TCA ACT TAT AAA

TTG AAG CCA AGT TAT CCT CCA ACA TAC AAA TCT AAA ACA AGT

TAC CCT CCT ACA TAT AAC AAA AAG ATC AGC TAT CCA TCA TCA

TAT AAA GCT AAG ACA AGT TAT CCC CCA GCA TAT AAA CCA ACA

AAC AGA TAT.

or a fragment of said sequence, said fragment encoding a protein capable of function as a bioadhesive after expression and upon hydroxylation and oxidation.

12. A DNA segment as claimed in claim 4, comprising the following DNA sequence:

CTA CCG

CCA GCA CCT CCT GCT CCT GCA TTT GCT CCT GCT CCT GCA CTT

GCA CCG GCT CCT CCA AAT CCT AAT CCT CCA AGT CCT CCG AGT

CCT CCG AGT CCA CCG ACT CCA CCG CCG ACT CCT CCA AGT CCA

CCA GCT CCT CCG AGT CCA CCA CCG AGT CCT CCG AAT CCA CCT

CCG AGT CCA CCT CCG AGT CCA CCG TTT CCT CCG GCT CCA CCT

CCG AGT CCA CCA TTT CCT CCG ACT TAT AAA GCA AAG CCA ACT

TAT AAA GCA AAG CCA ACT AAT CCT TCA ACG TAT AAA GCA AAG

CCA AGT TAT CCT CCA ACT TAT AAA GCA AAA CCA AGT TAT CCT

CCA ACT TAT AAA GCA AAA CCA AGT TAT CCT CCA ACG TAT AAA

GCA AAG CCA ACT TAT AAA ATA AAG CCA ACT TAT CCT TCA ACG

TAT AAA GCA AAG CCA ACT AAT CCT TCA ACG TAT AAA GCA AAG

CCA AGT TAT CCT CCA ACT TAT AAA GCA AAA CCA AGT TAT CCT

CCA ACT TAT AAA GCA AAA CCA AGT TAT CCT CCA ACG TAT AAA

GCA AAG CCA ACT TAT AAA ATA AAG CCA ACT TAT CCT TCA ACG

TAT AAA GCA AAG CCA ACT TAT AAA GCA AAG CCA ACT TAT CCT

CCA ACT TAT AAA GCA AAA CCA AGT TAT CCT CCA ACA TAT AAA

CCA AAG CCA AGT TAT CCT CCA ACT TAT AAA TCC AAG TCA ATA

TAT CCC TCT TCA TAC AAA CCT AAG AAA ACT TAT CCC CCC ACA

TAT AAA CCT AAA CTA ACC TAT CCT CCA ACA TAT AAA CCA AAG

CCA AGT TAT CCA CCA TCT TAT AAA CCT AAG ATT ACT TAT CCC

TCA ACT TAT AAA TTG AAG CCA AGT TAT CCT CCA ACA TAC AAA

TCT AAA ACA AGT TAC CCT CCT ACA TAT AAC AAA AAG ATC AGC

TAT CCA TCA TCA TAT AAA GCT AAG ACA AGT TAT CCC CCA GCA

TAT AAA CCA ACA AAC AGA TAT, or a fragment of said sequence, said fragment encoding a protein capable of function as a bioadhesive after expression and upon hydroxylation and oxidation.

13. A DNA segment as claimed in claim 4 comprising the following DNA sequence:

TAT AAA GCA AAA CCA AGT TAT CCT CCA ACT TAT AAA GCA AAG CCA ACT TAT AAA GCA AAG CCA ACT

AAT CCT TCA ACG TAT AAA GCA AAG CCA AGT TAT CCT CCA ACT TAT AAA GCA AAA CCA AGT TAT CCT CCA

ACT TAT AAA GCA AAA CCA AGT TAT CCT CCA ACG TAT AAA GCA AAG CCA ACT TAT AAA GCA AAG CCA

ACT TAT CCT TCA ACG TAT AAA GCA AAG CCA ACT TAT AAA GCA AAG CCA ACT TAT CCT CCA ACT TAT AAA

GCA AAA CCA AGT TAT CCT CCA ACA TAT AAA CCA AAG CCA AGT TAT CCT CCA ACT TAT AAA TCC AAG TCA

ATA TAT CCC TCT TCA TAC AAA CCT AAG AAA ACT TAT CCC CCC ACA TAT, or a fragment of said sequence, said fragment encoding a protein capable of function as a bioadhesive after expression and upon hydroxylation and oxidation.

14. A DNA segment as claimed in claim 4 comprising the following DNA sequence:

ACT TCA ACT TAT AAA GCA AAA CCA AGT TAT CCT CCA ACT TAT AAA GCA AAG CCA ACT TAC CCT TCA ACG

TAT AAA GCA AAA CCA AGT TAT CCT CCA ACT TAT AAA CCT AAG ATA AGT TAT CCT CCA ACT TAT AAA GCA

AAA CCA AGT TAT CCT CCA ACT TAT AAA GCA AAA CCA AGT TAT CCT CCA ACT TAT AAA GCA AAG CCA ACT

TAT AAA GCA AAG CCA ACT AAT CCT TCA ACG TAT AAA GCA AAG CCA AGT TAT, or a fragment of said sequence said fragment encoding a protein capable of function as a bioadhesive after expression and upon hydroxylation and oxidation.

15. A vector for expression of a bioadhesive precursor protein comprising:
(a) a DNA segment comprising codons which encode the native amino acid sequence of a bioadhesive precursor protein of a marine animal selected from the group consisting of mussels and barnacles, said protein being capable of function as a bioadhesive after expression and upon hydroxylation and oxidation, or an isolated DNA segment comprising codons which encode the native amino acid sequence of a fragment of said protein, said fragment being capable of function as a bioadhesive after expression and upon hydroxylation and oxidation; and
(b) a promoter and transcription initiation signals, operably linked to said DNA segment, which are capable of effecting microbial expression of said bioadheisve precursor protein.

16. A vector as claimed in claim 15 wherein the encoded bioadhesive precursor protein is from mussel.

17. A vector as claimed in claim 16, wherein the encoded bioadhesive precursor protein is of the mussel species *Mytilus edulis*.

18. A vector as claimed in claim 17, wherein the DNA segment (a) comprises codons for a bioadhesive precursor comprising the amino acid sequence:

Lys Leu Ser Ser Tyr Lys Pro Ile Lys Thr Thr Tyr Asn Ala Lys Thr Asn Tyr Pro Pro Val Tyr Lys Pro Lys Met Thr Tyr Pro Pro Thr

Tyr Lys Pro Lys Pro Ser Tyr Pro Pro Thr Tyr Lys Ser Lys Pro Thr Tyr Lys Pro Lys Ile Thr Tyr Pro Pro Thr Tyr Lys Ala Lys Pro

Ser Tyr Pro Pro Thr Tyr Lys Pro Lys Lys Thr Tyr Pro Pro Thr Tyr Lys Pro Lys Leu Thr Tyr Pro Pro Thr Tyr Lys Pro Lys Pro Ser

Tyr Pro Pro Thr Tyr Lys Ser Lys Pro Thr Tyr Lys Pro Lys Ile Thr Tyr Pro Pro Thr Tyr Lys Ala Lys Pro Ser Tyr Pro Pro Thr Tyr

Lys Pro Lys Lys Thr Tyr Pro Pro Thr Tyr Lys Pro Lys Leu Thr Tyr Pro Pro Thr Tyr Lys Pro Lys Ala Ser Tyr Pro Pro Thr Tyr Lys

Pro Lys Pro Ser Tyr Pro Pro Ser Tyr Lys Thr Lys Lys Thr Tyr Pro Pro Thr Tyr Lys Pro Lys Leu Thr Tyr Pro Pro Thr Tyr Lys Pro

Lys Pro Ser Tyr Pro Pro Ser Tyr Lys Pro Lys Lys Thr Tyr Pro Pro Thr Tyr Lys Pro Lys Leu Thr Tyr Pro Pro Thr Tyr Lys Ala Lys

Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro

Ser Tyr Pro Ser Thr Tyr Lys Ala Lys Pro Ser Tyr Pro Pro Thr Tyr Lys Ala Lys Pro Thr Tyr Lys Ala Lys Pro Thr Tyr Lys Ala Lys

Pro Thr Tyr Pro Ser Thr Tyr Lys Ala Lys Pro Thr Tyr Pro Pro Thr Tyr Lys Ala Lys Pro Ser Tyr Pro Pro Thr Tyr Lys Ala Lys Pro

Thr Tyr Lys Ala Lys Pro Thr Tyr Lys Ala Lys Pro Ser Tyr Pro Pro Thr Tyr Lys Ala Lys Pro Ser Tyr Pro Pro Thr Tyr Lys Ala Lys

Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Val Lys Pro

Thr Tyr Lys Ala Lys Pro Thr Tyr Pro Ser Thr Tyr Lys Ala Lys Pro Ser Tyr Pro Pro Thr Tyr Lys Ala Lys Pro Ser Tyr Pro Pro Thr

Tyr Lys Ala Lys Pro Ser Tyr Pro Pro Thr Tyr Lys Ala Lys Pro Ser Tyr Pro Pro Thr Tyr Lys Ala Lys Pro Thr Tyr Pro Ser Thr Tyr

Lys Ala Lys Pro Ser Tyr Pro Pro Thr Tyr Lys Pro Lys Ile Ser Tyr Pro Pro Thr Tyr Lys Ala Lys Pro Ser Tyr Pro Ser Thr Tyr Lys

Ala Lys Ser Ser Tyr Pro Pro Thr Tyr Lys Ala Lys Pro Ser Tyr Pro Pro Thr Tyr Lys Ala Lys Pro Thr Tyr Pro Ser Thr Tyr Lys Ala

-continued

Lys Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro

Pro Thr Tyr Lys Ala Lys Pro Thr Tyr Lys Ala Lys Pro Thr Tyr Lys Ala Lys Pro Thr Tyr Pro Ser Thr Tyr Lys Ala Lys Pro Ser Tyr

Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro

Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro

Thr Tyr Lys Ala Lys Pro Thr Tyr Lys Ala Lys Pro Thr Tyr Pro Ser Thr Tyr Lys Ala Lys Pro Ser Tyr Pro Pro Thr Tyr Lys Ala Lys

Pro Ser Tyr Pro Pro Thr Tyr Lys Ala Lys Pro Ser Tyr Pro Pro Thr Tyr Lys Ala Lys Pro Thr Tyr Lys Ala Lys Pro Thr Tyr Pro Ser

Thr Tyr Lys Ala Lys Pro Ser Tyr Pro Pro Thr His Lys Ala Lys Pro Thr Tyr Lys Ala Lys Pro Thr Tyr Pro Ser Thr Tyr Lys Ala Lys

Pro Thr Tyr Pro Ser Thr Asp Gly Ala Lys Ser, or a fragment of said sequence, said fragment encoding a protein capable of function as a bioadhesive after expression and upon hydroxylation and oxidation.

19. A vector as claimed in claim 17, wherein the DNA segment (a) comprises codons for a bioadhesive precursor comprising the amino acid sequence:

Lys Pro Lys Pro Ser Tyr Pro Pro Ser Tyr Lys

Pro Lys Thr Thr Tyr Pro Pro Thr Tyr Lys Pro Lys Ile Ser

Tyr Pro Pro Thr Tyr Lys Ala Lys Pro Ser Tyr Pro Ala Thr

Tyr Lys Ala Lys Pro Ser Tyr Pro Pro Thr Tyr Lys Ala Lys

Pro Ser Tyr Pro Pro Thr Tyr Lys Ala Lys Pro Ser Tyr Pro

Pro Thr Tyr Lys Ala Lys Pro Thr Tyr Lys Ala Lys Pro Thr

Tyr Pro Pro Thr Tyr Lys Ala Lys Pro Ser Tyr Pro Pro Thr

Tyr Lys Pro Lys Pro Ser Tyr Pro Pro Thr Tyr Lys Ser Lys

Ser Ile Tyr Pro Ser Ser Tyr Lys Pro Lys Lys Thr Tyr Pro

Pro Thr Tyr Lys Pro Lys Leu Thr Tyr Pro Pro Thr Tyr Lys

Pro Lys Pro Ser Tyr Pro Pro Ser Tyr Lys Pro Lys Ile Thr

Tyr Pro Ser Thr Tyr Lys Leu Lys Pro Ser Tyr Pro Pro Thr

Tyr Lys Ser Lys Thr Ser Tyr Pro Pro Thr Tyr Asn Lys Lys

Ile Ser Tyr Pro Ser Ser Tyr Lys Ala Lys Thr Ser Tyr Pro

Pro Ala Tyr Lys Pro Thr Asn Arg Tyr or a fragment of said sequence, said fragment encoding a protein capable of function as a bioadhesive after expression and upon hydroxylation and oxidation.

20. A vector as claimed in claim 17, wherein the DNA segment (a) comprises codons for a bioadhesive precursor protein comprising the amino acid sequence:

Leu Pro Pro Ala Pro Pro Ala Pro Ala Phe Ala Pro Ala Pro Ala

Leu Ala Pro Ala Pro Pro Asn Pro Asn Pro Pro Ser Pro Pro Ser

Pro Pro Ser Pro Pro Thr Pro Pro Pro Thr Pro Pro Ser Pro Pro

Ala Pro Pro Ser Pro Pro Pro Ser Pro Pro Asn Pro Pro Pro Ser

Pro Pro Pro Ser Pro Pro Phe Pro Pro Ala Pro Pro Pro Ser Pro

Pro Phe Pro Pro Thr Tyr Lys Ala Lys Pro Thr Tyr Lys Ala Lys

Pro Thr Asn Pro Ser Thr Tyr Lys Ala Lys Pro Ser Tyr Pro Pro

Thr Tyr Lys Ala Lys Pro Ser Tyr Pro Pro Thr Tyr Lys Ala Lys

Pro Ser Tyr Pro Pro Thr Tyr Lys Ala Lys Pro Thr Tyr Lys Ile

Lys Pro Thr Tyr Pro Ser Thr Tyr Lys Ala Lys Pro Thr Asn Pro

Ser Thr Tyr Lys Ala Lys Pro Ser Tyr Pro Pro Thr Tyr Lys Ala

Lys Pro Ser Tyr Pro Pro Thr Tyr Lys Ala Lys Pro Ser Tyr Pro

Pro Thr Tyr Lys Ala Lys Pro Thr Tyr Lys Ile Lys Pro Thr Tyr

Pro Ser Thr Tyr Lys Ala Lys Pro Thr Tyr Lys Ala Lys Pro Thr

Tyr Pro Pro Thr Tyr Lys Ala Lys Pro Ser Tyr Pro Pro Thr Tyr

Lys Pro Lys Pro Ser Tyr Pro Pro Thr Tyr Lys Ser Lys Ser Ile

Tyr Pro Ser Ser Tyr Lys Pro Lys Lys Thr Tyr Pro Pro Thr Tyr

Lys Pro Lys Leu Thr Tyr Pro Pro Thr Tyr Lys Pro Lys Pro Ser

Tyr Pro Pro Ser Tyr Lys Pro Lys Ile Thr Tyr Pro Ser Thr Tyr

Lys Leu Lys Pro Ser Tyr Pro Pro Thr Tyr Lys Ser Lys Thr Ser

Tyr Pro Pro Thr Tyr Asn Lys Lys Ile Ser Tyr Pro Ser Ser Tyr

Lys Ala Lys Thr Ser Tyr Pro Pro Ala Tyr Lys Pro Thr Asn Arg

Tyr or a fragment of said sequence, said fragment encoding a protein capable of function as a bioadhesive after expression and upon hydroxylation and oxidation.

21. A vector as claimed in claim 17 wherein the DNA segment (a) comprises codons for a bioadhesive precursor protein comprising the amino acid sequence:

Tyr Lys Ala Lys Pro Ser Tyr Pro Pro Thr Tyr Lys Ala Lys Pro

Thr Tyr Lys Ala Lys Pro Thr Asn Pro Ser Thr Tyr Lys Ala Lys

Pro Ser Tyr Pro Pro Thr Tyr Lys Ala Lys Pro Ser Tyr Pro Pro

Thr Tyr Lys Ala Lys Pro Ser Tyr Pro Pro Thr Tyr Lys Ala Lys

Pro Thr Tyr Lys Ala Lys Pro Thr Tyr Pro Ser Thr Tyr Lys Ala

Lys Pro Thr Tyr Lys Ala Lys Pro Thr Tyr Pro Pro Thr Tyr Lys

Ala Lys Pro Ser Tyr Pro Pro Thr Tyr Lys Pro Lys Pro Ser Tyr

Pro Pro Thr Tyr Lys Ser Lys Ser Ile Tyr Pro Ser Ser Tyr Lys

Pro Lys Lys Thr Tyr Pro Pro Thr Tyr, or a fragment of said sequence, said fragment encoding a protein capable of function as a bioadhesive after expression and upon hydroxylation and oxidation.

22. A vector as claimed in claim 17 wherein the DNA segment (a) comprises codons for a bioadhesive precursor protein comprising the amino acid sequence:

Thr Ser Thr Tyr Lys Ala Lys Pro Ser Tyr Pro Pro Thr Tyr Lys
Ala Lys Pro Thr Tyr Pro Ser Thr Tyr Lys Ala Lys Pro Ser Tyr
Pro Pro Thr Tyr Lys Pro Lys Ile Ser Tyr Pro Pro Thr Tyr Lys
Ala Lys Pro Ser Tyr Pro Pro Thr Tyr Lys Ala Lys Pro Ser Tyr
Pro Pro Thr Tyr Lys Ala Lys Pro Thr Tyr Lys Ala Lys Pro Thr
Asn Pro Ser Thr Tyr Lys Ala Lys Pro Ser Tyr, or a fragment of said sequence, said fragment encoding a protein capable of function as a bioadhesive after expression and upon hydroxylation and oxidation.

23. A vector as claimed in claim 17, wherein the DNA segment (a) consists of the following sequence of bases:

AAG CTG TCA TCT TAC AAA CCT ATT AAG ACA ACA
TAT AAT GCA AAG ACA AAT TAT CCA CCA GTT TAT
AAA CCT AAG ATG ACT TAT CCT CCT ACA TAC AAA
CCA AAG CCC AGT TAT CCT CCA ACA TAT AAA TCA
AAG CCC ACA TAC AAA CCT AAG ATA ACA TAC CCT
CCA ACT TAT AAA GCA AAG CCC AGT TAT CCT CCA
ACA TAT AAA CCT AAG AAA ACT TAT CCC CCC ACA
TAT AAA CCT AAA CTA ACC TAT CCT CCT ACA TAC
AAA CCA AAG CCC AGT TAT CCT CCA ACA TAT AAA
TCA AAG CCC ACA TAC AAA CCT AAG ATA ACA TAC
CCT CCA ACA TAT AAA GCA AAG CCA AGT TAT CCT
CCT ACA TAT AAA CCT AAG AAA ACT TAT CCC CCC
ACA TAT AAA CCT AAA CTA ACC TAT CCT CCT ACA
TAT AAA CCA AAG GCC AGT TAT CCT CCA ACA TAT
AAA CCA AAA CCA AGT TAT CCC CCT TCA TAT AAA
ACT AAG AAA ACT TAT CCC CCC ACA TAT AAA CCT
AAA CTA ACC TAT CCT CCT ACA TAT AAA CCA AAA
CCA AGT TAT CCC CCT TCA TAC AAA CCT AAG AAA
ACT TAT CCC CCC ACA TAT AAA CCT AAA CTA ACC
TAT CCT CCT ACA TAT AAA GCA AAG CCA AGT TAT
CCT CCA ACA TAT AAA GCA AAA CCA AGT TAT CCT
CCA ACT TAT AAA GCA AAA CCA AGT TAT CCT CCA
ACA TAT AAA GCA AAA CCA AGT TAT CCT TCA ACT
TAT AAA GCA AAA CCA AGT TAT CCT CCA ACT TAT
AAA GCA AAG CCA ACT TAT AAA GCA AAG CCA ACT
TAT AAA GCA AAG CCA ACT TAT CCT TCA ACG TAT
AAA GCA AAG CCA ACT TAT CCT CCA ACT TAT AAA
GCA AAA CCA AGT TAT CCT CCA ACT TAT AAA GCA
AAG CCA ACT TAT AAA GCA AAG CCA ACT TAT AAA
GCA AAG CCA AGT TAT CCT CCA ACT TAT AAA GCA
AAA CCA AGT TAT CCT CCA ACT TAT AAA GCA AAG
CCA AGT TAT CCT CCA ACG TAT AAA GCA AAG CCA
AGT TAT CCT CCA ACT TAT AAA GCA AAA CCA AGT
TAT CCT CCA ACT TAT AAA GTA AAG CCA ACA TAT
AAA GCA AAA CCA ACT TAT CCT TCA ACG TAT AAA
GCA AAG CCA AGT TAT CCT CCA ACT TAT AAA GCA
AAA CCA AGT TAT CCT CCA ACT TAT AAA GCA AAA
CCA AGT TAT CCT CCA ACG TAT AAA GCA AAA CCA
AGT TAT CCT CCA ACT TAT AAA GCA AAA CCA ACT
TAT CCT TCA ACG TAT AAA GCA AAA CCA AGT TAT
CCT CCA ACT TAT AAA CCT AAA ATA AGT TAT CCT
CCA ACT TAT AAA GCA AAA CCA AGT TAT CCT TCA
ACT TAT AAA GCA AAA TCA AGT TAT CCT CCA ACT
TAT AAA GCA AAA CCA AGT TAT CCT CCA ACT TAT
AAA GCA AAG CCA ACT TAT CCT TCA ACG TAT AAA
GCA AAG CCA ACT TAT AAA GCA AAG CCA AGT TAT
CCT CCA ACG TAT AAA GCA AAG CCA AGT TAT CCT
CCA ACT TAT AAA GCA AAA CCC AGT TAT CCT CCA
ACT TAT AAA GCA AAG CCA ACT TAT AAA GCA AAG
CCA ACT TAT AAA GCA AAG CCA ACT TAT CCT TCA
ACG TAT AAA GCA AAG CCA AGT TAT CCT CCA ACT
TAT AAA GCA AAA CCA AGT TAT CCT CCA ACT TAT
AAA GCA AAA CCA AGT TAT CCT CCA ACT TAT AAA
GCA AAA CCA AGT TAT CCT CCA ACT TAT AAA GCA
AAG CCA AGT TAT CCT CCA ACG TAT AAA GCA AAG
CCA AGT TAT CCT CCA ACT TAT AAA GCA AAA CCA
AGT TAT CCT CCA ACT TAT AAA GCA AAG CCA ACT
TAT AAA GCA AAG CCA ACT TAT CCT TCA ACG TAT
AAA GCA AAG CCA AGT TAT CCT CCA ACT TAT AAA
GCA AAA CCA AGT TAT CCT CCA ACT TAT AAA GCA
AAA CCA AGT TAT CCT CCA ACT TAT AAA GCA AAA
CCA ACT TAT AAA GCA AAG CCA ACT TAT CCT TCA
ACG TAT AAA GCA AAA CCA AGT TAT CCT CCA ACT
CAT AAA GCA AAA CCA ACT TAT AAA GCA AAG CCA
ACT TAT CCT TCA ACT TAT AAA GCA AAA CCA ACT
TAT CCT TCA ACG GAT GGA GCA AAA TCA.

or a fragment of said sequence, said fragment encoding a protein capable of function as a bioadhesive after expression and upon hydroxylation and oxidation.

24. A vector as claimed in claim 17, wherein the DNA segment (a) consists of the following sequence of bases:

AAA CCA AAA CCA AGT TAT CCA CCA TCT TAT AAA

CCT AAA ACA ACT TAT CCT CCA ACT TAT AAA CCT

AAG ATA AGT TAT CCT CCA ACT TAT AAA GCA AAA

CCA AGT TAT CCA GCA ACT TAT AAA GCA AAA CCA

AGT TAT CCT CCA ACT TAT AAA GCA AAA CCA AGT

TAT CCT CCA ACT TAT AAA GCA AAA CCA AGT TAT

CCT CCA ACT TAT AAA GCA AAG CCA ACT TAT AAA

GCA AAG CCA ACT TAT CCT CCA ACT TAT AAA GCA

AAA CCA AGT TAT CCT CCA ACA TAT AAA CCA AAG

CCA AGT TAT CCT CCA ACT TAT AAA TCC AAG TCA

ATA TAT CCC TCT TCA TAC AAA CCT AAG AAA ACT

TAT CCC CCC ACA TAT AAA CCT AAA CTA ACC TAT

CCT CCA ACA TAT AAA CCA AAG CCA AGT TAT CCA

CCA TCT TAT AAA CCT AAG ATT ACT TAT CCC TCA

ACT TAT AAA TTG AAG CCA AGT TAT CCT CCA ACA

TAC AAA TCT AAA ACA AGT TAC CCT CCT ACA TAT

AAC AAA AAG ATC AGC TAT CCA TCA TCA TAT AAA

GCT AAG ACA AGT TAT CCC CCA GCA TAT AAA CCA

ACA AAC AGA TAT, or a fragment of said sequence, said fragment encoding a protein capable of function as a bioadhesive after expression and upon hydroxylation and oxidation.

25. A vector as claimed in claim 17, wherein the DNA segment (a) consists of the following sequence of bases:

CTA CCG CCA GCA CCT CCT GCT CCT GCA TTT GCT

CCT GCT CCT GCA CTT GCA CCG GCT CCT CCA AAT

CCT AAT CCT CCA AGT CCT CCG AGT CCT CCG AGT

CCA CCG ACT CCA CCG CCG ACT CCT CCA AGT CCA

CCA GCT CCT CCG AGT CCA CCA CCG AGT CCT CCG

AAT CCA CCT CCG AGT CCA CCT CCG AGT CCA CCG

TTT CCT CCG GCT CCA CCT CCG AGT CCA CCA TTT

CCT CCG ACT TAT AAA GCA AAG CCA ACT TAT AAA

GCA AAG CCA ACT AAT CCT TCA ACG TAT AAA GCA

AAG CCA AGT TAT CCT CCA ACT TAT AAA GCA AAA

CCA AGT TAT CCT CCA ACT TAT AAA GCA AAA CCA

AGT TAT CCT CCA ACG TAT AAA GCA AAG CCA ACT

TAT AAA ATA AAG CCA ACT TAT CCT TCA ACG TAT

AAA GCA AAG CCA ACT AAT CCT TCA ACG TAT AAA

GCA AAG CCA AGT TAT CCT CCA ACT TAT AAA GCA

AAA CCA AGT TAT CCT CCA ACT TAT AAA GCA AAA

CCA AGT TAT CCT CCA ACG TAT AAA GCA AAG CCA

ACT TAT AAA ATA AAG CCA ACT TAT CCT TCA ACG

TAT AAA GCA AAG CCA ACT TAT AAA GCA AAG CCA

ACT TAT CCT CCA ACT TAT AAA GCA AAA CCA AGT

TAT CCT CCA ACA TAT AAA CCA AAG CCA AGT TAT

CCT CCA ACT TAT AAA TCC AAG TCA ATA TAT CCC

TCT TCA TAC AAA CCT AAG AAA ACT TAT CCC CCC

ACA TAT AAA CCT AAA CTA ACC TAT CCT CCA ACA

TAT AAA CCA AAG CCA AGT TAT CCA CCA TCT TAT

AAA CCT AAG ATT ACT TAT CCC TCA ACT TAT AAA

TTG AAG CCA AGT TAT CCT CCA ACA TAC AAA TCT

AAA ACA AGT TAC CCT CCT ACA TAT AAC AAA AAG

ATC AGC TAT CCA TCA TCA TAT AAA GCT AAG ACA

AGT TAT CCC CCA GCA TAT AAA CCA ACA AAC AGA

TAT, or a fragment of said sequence, said fragment encoding a protein capable of function as a bioadhesive after expression and upon hydroxylation and oxidation.

26. A vector as claimed in claim 17, wherein the DNA segment (a) comprises the following sequence of bases:

TAT AAA GCA AAA CCA AGT TAT CCT CCA ACT TAT

AAA GCA AAG CCA ACT TAT AAA GCA AAG CCA ACT

AAT CCT TCA ACG TAT AAA GCA AAG CCA AGT TAT

CCT CCA ACT TAT AAA GCA AAA CCA AGT TAT CCT

CCA ACT TAT AAA GCA AAA CCA AGT TAT CCT CCA

ACG TAT AAA GCA AAG CCA ACT TAT AAA GCA AAG

CCA ACT TAT CCT TCA ACG TAT AAA GCA AAG CCA

ACT TAT AAA GCA AAG CCA ACT TAT CCT CCA ACT

TAT AAA GCA AAA CCA AGT TAT CCT CCA ACA TAT

AAA CCA AAG CCA AGT TAT CCT CCA ACT TAT AAA

TCC AAG TCA ATA TAT CCC TCT TCA TAC AAA CCT

AAG AAA ACT TAT CCC CCC ACA TAT, or a fragment of said sequence, said fragment encoding a protein capable of function as a bioadhesive after expression and upon hydroxylation and oxidation.

27. A vector as claimed in claim 17, wherein the DNA segment (a) comprises the following sequence of bases:

ACT TCA ACT TAT AAA GCA AAA CCA AGT TAT CCT

CCA ACT TAT AAA GCA AAG CCA ACT TAC CCT TCA

ACG TAT AAA GCA AAA CCA AGT TAT CCT CCA ACT

TAT AAA CCT AAG ATA AGT TAT CCT CCA ACT TAT

AAA GCA AAA CCA AGT TAT CCT CCA ACT TAT AAA

GCA AAA CCA AGT TAT CCT CCA ACT TAT AAA GCA

AAG CCA ACT TAT AAA GCA AAG CCA ACT AAT CTT

-continued

TCA ACG TAT AAA GCA AAG CCA AGT TAT, or a fragment of said sequence, said fragment encoding a protein capable of function as a bioadhesive after expression and upon hydroxylation and oxidation.

28. A microorganism, said microorganism containing the expression vector of claim 15, 16, 17, 18, 19, 20, 21, 22, 23, 24 25, 26 or 27, and said microorganism being capable of expressing a bioadhesive precursor protein.

29. The microorganism of claim 28, wherein said microorganism is E. coli.

30. The microorganism of claim 28, wherein said microorganism is S. cerevisiae.

* * * * *

UNITED STATES PATENT AND TRADEMARK OFFICE
CERTIFICATE OF CORRECTION

PATENT NO. : 5,049,504

DATED : September 17, 1991

INVENTOR(S) : Kathy J. Maugh, et al

It is certified that error appears in the above-identified patent and that said Letters Patent is hereby corrected as shown below:

Title page, item [75], delete, "Tena Wei"

In column 4, in line 12, delete "margine" and replace therefor
-- marine --;

in line 14, please insert -- In one embodiment, the bioadhesive precursor protein DNA sequence comprises the codons: --

In column 5, in line 4 after "TCA," insert -- or a fragment thereof. --;

in line 48 after "ser," insert -- or a fragment thereof.--.

In column 10, in line 52, delete the hyphen after "thereof-".

In column 13, in line 17 delete "reated" and replace therewith
--created --;

in line 28, delete "LbaI" and replace therewith
-- XbaI--.

In column 17, in line 19, delete "glassdistilled" and replace therewith -- glass-distilled --;

in line 61, delete "0 25" and replace therewith
-- 0.25 --;

in line 62, delete "0 1" and replace therewith
-- 0.1 --.

In column 18, in line 23, insert a period between the words "nuclease" and "The";

in line 47, delete "M H" and replace therewith
-- M $H_2SO_4$ --.

In column 19, in line 24, delete "qamma" and insert therewith
-- gamma --.

UNITED STATES PATENT AND TRADEMARK OFFICE
CERTIFICATE OF CORRECTION

PATENT NO. : 5,049,504

DATED : September 17, 1991

INVENTOR(S) : Kathy J. Maugh, et al

It is certified that error appears in the above-identified patent and that said Letters Patent is hereby corrected as shown below:

In column 20, in line 50, insert a period after the word "plate".

In column 21, in line 68, insert a period between the words "residues" and "These".

In column 22, in line 12, insert a period between "cDNA" and "This";

in line 56, delete "[alpha-32P]" and replace therewith -- [alpha-$^{32}$P];

in line 56, insert a period between the words "label" and "Hybridization";

in line 61, delete "hybrid-zation-positive" and replace therewith --hybridization-positive --.

In column 23, in line 45, delete "Mandol" and replace therein -- Mandel --.

In column 25, in line 44, delete "step 5" and replace therewith -- step 6 --.

In column 26, in line 54, delete "12 x1" and replace therein "12 ml";

in line 63, "The following fermentation" should start a new line.

UNITED STATES PATENT AND TRADEMARK OFFICE
CERTIFICATE OF CORRECTION

PATENT NO. : 5,049,504

DATED : September 17, 1991

INVENTOR(S) : Kathy J. Maugh, et al

It is certified that error appears in the above-identified patent and that said Letters Patent is hereby corrected as shown below:

In column 27, in line 16, delete "$6H_2$" and replace therein
-- $6H_2O$ --;
in line 26, delete "Hcl" and replace therein
-- HCl --;
in line 57, insert a period between the words "centrifugation" and "Washing";
in line 58, insert a period between the words "clear" and "The".

In column 29, in line 47, delete "30:337-346" and replace therein -- 130:337-346 --.

In column 32, in line 66, delete "decaand" and replace therein -- deca- and --.

In column 33, in line 65, delete "initia" and replace therewith -- initial --.

Signed and Sealed this

Fifteenth Day of June, 1993

*Attest:*

MICHAEL K. KIRK

*Attesting Officer*   Acting Commissioner of Patents and Trademarks